US011090396B2

(12) United States Patent
Stewart

(10) Patent No.: US 11,090,396 B2
(45) Date of Patent: *Aug. 17, 2021

(54) COMPOUNDS AND METHODS FOR THE DETECTION OF TRPV-6 CANCERS AND DRUG DELIVERY

(71) Applicant: SORICIMED BIOPHARMA INC., Moncton (CA)

(72) Inventor: John M. Stewart, Sackville (CA)

(73) Assignee: Soricimed Biopharma Inc., Moncton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/046,786

(22) Filed: Jul. 26, 2018

(65) Prior Publication Data
US 2019/0209717 A1 Jul. 11, 2019

Related U.S. Application Data

(63) Continuation of application No. 14/579,157, filed on Dec. 22, 2014, now Pat. No. 10,064,964, which is a continuation of application No. 12/824,935, filed on Jun. 28, 2010, now abandoned.

(60) Provisional application No. 61/244,634, filed on Sep. 22, 2009, provisional application No. 61/220,833, filed on Jun. 26, 2009.

(51) Int. Cl.
| *A61K 51/08* | (2006.01) |
| *A61K 51/10* | (2006.01) |
| *A61K 45/06* | (2006.01) |
| *A61K 49/00* | (2006.01) |
| *A61K 49/14* | (2006.01) |
| *A61K 49/18* | (2006.01) |
| *B82Y 5/00* | (2011.01) |
| *C07K 16/28* | (2006.01) |
| *G01N 33/574* | (2006.01) |
| *G01N 33/68* | (2006.01) |
| *A61K 47/64* | (2017.01) |
| *A61K 47/68* | (2017.01) |
| *A61K 31/337* | (2006.01) |
| *A61K 33/24* | (2019.01) |
| *A61K 39/00* | (2006.01) |
| *A61K 49/16* | (2006.01) |

(52) U.S. Cl.
CPC ........ *A61K 51/1093* (2013.01); *A61K 31/337* (2013.01); *A61K 33/24* (2013.01); *A61K 39/0005* (2013.01); *A61K 45/06* (2013.01); *A61K 47/64* (2017.08); *A61K 47/6803* (2017.08); *A61K 49/0032* (2013.01); *A61K 49/0056* (2013.01); *A61K 49/0058* (2013.01); *A61K 49/14* (2013.01); *A61K 49/16* (2013.01); *A61K 49/1866* (2013.01); *B82Y 5/00* (2013.01); *C07K 16/28* (2013.01); *G01N 33/57415* (2013.01); *G01N 33/57434* (2013.01); *G01N 33/57449* (2013.01); *G01N 33/57492* (2013.01); *G01N 33/6872* (2013.01); *G01N 2333/705* (2013.01)

(58) Field of Classification Search
CPC ........ A61K 38/08; A61K 38/00; A61K 38/03; A61K 38/02; A61K 38/04; A61K 38/16; A61K 38/10; A61K 51/00; A61K 51/08; A61K 31/00; A61K 2121/00; A61K 2123/00; A61K 49/14; A61K 51/1093; A61K 47/00; A61K 47/64; A61K 47/6803; A61K 31/337; A61K 33/24; A61K 39/00; A61K 39/0005; A61K 49/00; A61K 49/16; A61K 45/00; A61K 45/06; A61K 49/0032; A61K 49/0056; A61K 49/0058; A61K 49/1866; A61K 51/088; G01N 33/57492; G01N 33/57415; G01N 33/57434; G01N 33/57449; G01N 33/6872; G01N 2333/705; B82Y 5/00; C07K 16/28
USPC .......... 424/1.11, 1.49, 1.65, 1.69, 1.81, 1.85, 424/1.89, 9.1, 9.2, 9.3, 9.4, 9.5, 9.6; 534/7, 10–16; 514/1.11, 19.2, 19.3, 19.4, 514/19.5, 19.6; 530/300
See application file for complete search history.

(56) References Cited

U.S. PATENT DOCUMENTS

| 5,424,286 | A | 6/1995 | Eng |
| 6,326,020 | B1 | 12/2001 | Kohane et al. |
| 6,534,642 | B1 | 3/2003 | Hediger et al. |
| 6,946,475 | B1 | 9/2005 | Gray et al. |
| 7,119,168 | B2 * | 10/2006 | Stewart .............. A61K 38/1709 530/350 |
| 7,205,108 | B2 | 4/2007 | Wissenbach |

(Continued)

FOREIGN PATENT DOCUMENTS

| EP | 1165508 | 6/2004 |
| JP | 10-236963 | 9/1998 |

(Continued)

OTHER PUBLICATIONS (Author Unknown),"The venom of the shrew maybe the new Botox", National Post, Science Section, Biochemistry, Dec. 20, 2002.

(Continued)

*Primary Examiner* — D. L. Jones
(74) *Attorney, Agent, or Firm* — Cooley LLP

(57) ABSTRACT

Compounds containing TRPV6-binding peptides and their use in the detection and diagnosis of cancer are described. Also described are methods for detecting and staging cancer that use the compounds of the invention. Compounds containing TRPV6-binding peptides are useful for the delivery of diagnostic and therapeutic agents to cells or tumors that express TRPV6.

14 Claims, 22 Drawing Sheets

Specification includes a Sequence Listing.

(56) References Cited

U.S. PATENT DOCUMENTS

| | | | | |
|---|---|---|---|---|
| 7,273,850 B2* | 9/2007 | Stewart | ............. | A61K 38/1709 514/17.4 |
| 7,485,622 B2* | 2/2009 | Stewart | ................. | C07K 14/47 514/1.1 |
| 7,745,588 B2* | 6/2010 | Stewart | ............. | A61K 38/1709 530/300 |
| 8,003,754 B2* | 8/2011 | Stewart | ............. | A61K 38/1709 530/300 |
| 8,211,857 B2* | 7/2012 | Stewart | ............. | C07K 14/4703 514/17.4 |
| 8,338,136 B2* | 12/2012 | Stewart | ............. | A61K 38/1709 435/71.1 |
| 8,618,058 B2* | 12/2013 | Stewart | ............. | C07K 14/4703 514/19.3 |
| 8,673,858 B2* | 3/2014 | Stewart | ............. | A61K 38/1709 514/18.6 |
| 8,962,817 B2* | 2/2015 | Stewart | .................... | C07K 7/06 536/23.1 |
| 9,303,077 B2* | 4/2016 | Stewart | ............. | C07K 14/4703 |
| 10,058,587 B2* | 8/2018 | Stewart | ................. | C07K 16/18 |
| 10,064,964 B2* | 9/2018 | Stewart | ............. | A61K 39/0005 |
| 2010/0305029 A1 | 12/2010 | Stewart et al. | | |
| 2010/0329983 A1 | 12/2010 | Stewart | | |
| 2012/0316119 A1 | 12/2012 | Stewart | | |
| 2015/0182644 A1 | 7/2015 | Stewart | | |
| 2017/0020835 A1 | 1/2017 | Chang | | |
| 2020/0384069 A1 | 12/2020 | Stewart | | |

FOREIGN PATENT DOCUMENTS

| | | |
|---|---|---|
| WO | WO 2004/046178 | 6/2004 |
| WO | WO 2009/114943 | 9/2009 |
| WO | WO 2019/108920 A1 | 6/2019 |

OTHER PUBLICATIONS

Aalders, J.G et al. "Endometrial cancer—revisiting the importance of pelvic and para aortic lymph nodes." Gynecol Oncol., Jan. 2007;104(1):222-31. Epub Nov. 28, 2006.

Agnes R.S. et al. "Structure-activity relationships of bifunctional peptides based on overlapping parmacophores and opioid and cholescytokinin receptors." Journal of Medicinal Chemistry, 2006, 49: 2868-2875.

Bodding M., Fecher-Trost C, Flockerzi V. "Store-operated Ca2+ Current and TRPV6 Channels in Lymph Node Prostate Cancer Cells." J Biol Chem, 2003, 278 (51): 50872-50879.

Bodding, M. "TRP proteins and cancer." Cellular Signalling, 2007, 19: 617-624.

Bolanz, K. et al. "The role of TRPV6 in breast carcinogenesis." Mol Cancer Ther, Feb. 2008, 7(2):271-279. eISSN: 1538-8514.

Bowen, C.V. et al. "In vivo detection of human TRPV6-rich tumors with anti-cancer peptides derived from soricidin." PLOS ONE, Mar. 15, 2013, vol. 8, No. 3, e58866(p. 1-11).

Cai, Z. et al., "Solution Structure of BmBKTx1, a New Bk.sub.CA.sup.1 Channel Blocker from the Chinese Scorpion *Buthus martensi* Karsch", Biochemistry, vol. 43, No. 13, pp. 3764-3771, 2004.

Christenbury, P., "A Study of the Ecology of Blarina brevicaudia in North Carolina and of the Effect of Shrew Toxin on the Liver and Kidneys of Mice". A thesis submitted to the Graduate Faculty of Wake Forest College in partial fulfillment of the requirements for the degree of Master of Arts in the Department of Biology, Aug. 1966.

Dekker, E. et al. "The epithelial calcium channels, TRPV5 and TRPV6: from identification towards regulation", Cell Calcium, vol. 33, pp. 497-507, 2003.

Dufton, M., "Venomous Mammals", Pharmac. Ther., vol. 53, pp. 199-215, 1992.

Ellis, S. et al., "Properties of a Toxin From the Salivary Gland of the Shrew, *Blarina brevicauda*", The Journal of Pharmacology & Experimental Therapeutics, vol. 114, No. 2, pp. 127-137, 1955.

Fixemer, T. et al. "Expression of the Ca+2-selective cation channel TRPV6 in human prostate cancer: a novel prognostic marker for tumor progression." Oncogene, 2003, 22: 7858-7861.

George, S. et al., "*Blarina brevicauda*", Mammalian Species, No. 261, pp. 1-9, 3 Figures, 1986.

Hoenderop, J.G.J. et al. "Epithelial Ca2+ and Mg2+ Channels in Health and Disease." J_ Am. Soc. Nephrol., 2005, 16: 15-26.

Kita, M. et al., "Blarina toxin, a mammalian lethal venom from the short-tailed shrew *Blarina brevicauda*: Isolation and characterization", Proceedings of the National Academy of Sciences of the United States of America, vol. 101, No. 20, pp. 7542-7547, 2004.

Lecchi, P. et al., "The Structure of Synenkephalin (Pro-Enkephalin .sub.1-73) Is Dictated by Three Disulfide Bridges", Biochemical and Biophysical Research Communications, vol. 232, pp. 800-805, 1997.

Lee, W.J. et al. "Calcium transport and signaling in the mammary gland: Targets for breast cancer." Biochim. Biophys. Acta, 2006, 1765: 235-255.

Lehen'Kyi, V. et al. "TRPV6 channel controls prostate cancer cell proliferation via Ca2+/NFAT-dependent pathways." Oncogene, 2007, 26: 7380-7385.

Lehen'Kyi, V. et al. "TRPV6 is a Ca2+ entry channel essential for Ca2+-induced differentiation of human keratinocytes." J Biol Chem, 2007, 282(31):22582-22591. eISSN: 1083-351X.

Lyshchik A. et al. "Cervical lymph node metastases: diagnosis at sonoelastography—initial experience." Radiology, Apr. 2007; 243 (1):258-67. Epub Feb. 9, 2007.

Ma, J., et al. "Retropharyngeal lymph node metastasis in nasopharyngeal carcinoma: prognostic value and staging categories." Clin Cancer Res. Mar. 1, 2007:13(5):1445-52.

Martin, I., "Venom of the Short-Tailed Shrew (*Blarina brevicauda*) as an Insect Immobilizing Aged", Journal of Mammalogy, vol. 62, No. 1, pp. 189-192, 1978.

Montell, C., "The venerable inveterate invertebrate TRP channels", Cell Calcium, vol. 33, pp. 409-417, 2003.

Mount Allison University, "Potent Peptide Paraly1ic Aged", Version 1, Jun. 2003.

Mount Allison University, "Potent Peptide Paraly1ic Aged", Version 2, Jul. 2003.

Mujoomdar A. et al. "Clinical predictors of metastatic disease to the brain from non-small cell lung carcinoma: primary tumor size, cell type, and lymph node metastases." Radiology, Mar. 2007; 242(3):882-8. Epub Jan. 17, 2007.

Nilius, B. et al. "Transient Receptor Potential Cation Channels in Disease." Physiol. Rev., 2007, 97: 165-217.

Pearson, O., "On the cause and nature of poisonous action produced by the bite of a shrew (*Blarina brevicauda*," Journal of Mammalogy, pp. 159-166, (1942).

Peng, J. et al. "CaT1 Expression Correlates with Tumor Grade in Prostate Cancer", Biochemical and Biophysical Research Communications, vol. 282, pp. 729-734, 2001.

Peng, J_ et al., "Human Calcium Transport Protein CaT1", Biochemical and Biophysical Research Communications, vol. 278, pp. 326-332, 2000.

Pigozzi, D. et al. "Calcium store contents control the expression of TRPC1, TRPC3 and TRPV6 in LnCaP prostate cancer cell line." Cell Calcium, 2006, 39: 401-415.

Pohl, M. et. al., "Molecular Cloning of the Helodermin and Exendin-4 cDNAs in the Lizard", The Journal of Biological Chemistry, vol. 273, No. 16, pp. 9778-9784, 1998.

Prevarskaya, N. et al. "TRP channels in cancer." Biochim. Biophys. Acta, 2007, 1772: 937-946.

Prevarskaya, N., et al. "Differential role of TRP channels in prostate cancer." Biochem. Soc. Trans., 2007, 35: 133-135.

Prevarskaya, N., et al. "Ion channels in death and differentiation of prostate cancer cells." Cell Death and Differentiation, 2007, 14: 1295-1304.

Pucek, M., Chemistry and Pharmacology of Insertivore Venoms, Chapter 3 of Venomous Animals and Their Venoms edited by W. Bucherl, Academic Press, New York—London, pp. 43-50, 1968.

Schwarz, E.G., et al. "TRPV6 potentiates calcium-dependent cell proliferation." Cell Calcium, 2006, 39: 163-173.

(56) References Cited

OTHER PUBLICATIONS

Semenova, S. et al. "Endogenous expression of TRPV5 and TRPV6 calcium channels in human leukemia K562 cells." Am. J. Physiol. Cell Physiol., 2009, 296: C1098-C1104. (published online Mar. 18, 2009, hardcopy in May 2009.).
Smart, P., "Shrew Saliva Spells Relief? Prof. Jack Stewart makes breakthrough medical discovery", the argosy, Jan. 16, 2003.
Soricimed (www.soricimed.com), 2013, Introduction and Pain Treatment section (2 pages).
Sternfeld, L. et al. "Identification of tyrosines in the putative regulatory site of the Ca2+ channel TRPV6." Cell Calcium, 2007, 42:91-102. eISSN: 1532-1991.
Stewart, J.M. et al. "A novel peptide inhibitor of TRPV6 shows activity against ovarian cancer in vitro and in vivo." Poster and Abstract presented at TRP Meeting, Sep. 26-27, 2009, Karolinska Institute!, Stockholm.
Stewart, J.M., and Roy, F. "News Release: BioProspecting and Atlantic Cancer Research Institute established formal collaboration to develop early diagnostic for ovarian cancer." BioProspecting NB, Inc. and Atlantic Cancer D Research Institute, Oct. 20, 2009.
Supplementary European Search Report and Written Opinion completed Sep. 1, 2015 for corresponding European Patent Application No. 10791109.
Thebault, S. et al. "Differential Role of Transient Receptor Potential Channels in Ca2+ Entry and Proliferation of Prostate Cancer Epithelial Cells." Cancer Res., 2006, 66(4): 2038-2047.
Tomasi, T., "Function of Venom in the Short-Tailed Shrew *Blarina brevicauda*", Journal of Mammalogy, vol. 59, No. 4, pp. 852-854, 1978.
Vanden Abeele, F. et al. "Store-operated Ca2+ channels in prostate cancer epithelial cells: function, regulation and role in carcinogenesis." Cell Calcium, 2003, 33: 357-373.
Veness M.J. et al. "Cutaneous head and neck squamous cell carcinoma metastatic to parotid and cervical lymph nodes." Head Neck . . . Jul. 2007;29(7):621-31.
Vernooij F. et al. "Lymph node recurrence following stage IA vu Ivar carcinoma: two cases and a short overview of literature." Int J Gynecol Cancer., Mar.-Apr. 2007;17(2):517-20. Epub Feb. 19, 2007.
Vriens, J. et al. "Pharmacology of vanilloid transient receptor potential cation channels." Molecular Pharmacology, 2009, 75 (6): 1262-1279. (published online Mar. 18, 2009; in paper journal Jun. 2009.).
Wind J. et al. "A systematic review on the significance of extracapsular lymph node involvement in gastrointestinal malignancies." Eur J Surg Oncol., May 2007; 33(4):401-8. Epub Dec. 15, 2006.
Wissenbach, U. et al. "Expression of CaT-like, a Novel Calcium-selective Channel, Correlates with the Malignancy of Prostate Cancer." J. Biol. Chem., 2001, 276: 22, 19461-19468.
Wissenbach, U. et al. "TRPV6 and prostate cancer: cancer growlh beyond the prostate correlates with increased TRPV6 Ca2+ channel expression." Biochem. Biophys. Res. Comm., 2004, 322: 1359-1363.
Wissenbach, U. et al. "TRPV6." HEP, 2007, 179: 221-234.
Yamamoto T. et al. "A structure-activity relationship study of combinatorial synthetic approach of C-terminal modified bifunctional peptides that are dell/mu opioid receptor agonists and neurokinin 1 receptor antagonists." Journal of Medicinal Chemistry, Mar. 13, 2008; 51(5): 1369-1376, epub, Feb. 12, 2008.
Zhuang, L. et al., "Calcium-Selective Ion Channel, CaT1, Is Apically Localized in Gastrointestinal Tract Epithelia and Is Aberrantly Expressed in Human Malignancies", Laboratory Investigation, vol. 82, No. 12, pp. 1755-1764, 2002.
Restriction Requirement dated Jun. 28, 2012 for U.S. Appl. No. 12/824,935.
Response dated Aug. 23, 2012 for U.S. Appl. No. 12/824,935.
Office Action dated Oct. 16, 2012 for U.S. Appl. No. 12/824,935.
Response dated Jan. 11, 2013 for U.S. Appl. No. 12/824,935.
Office Action dated Jan. 24, 2013 for U.S. Appl. No. 12/824,935.
Response and Request for Continued Examination dated Apr. 19, 2013 for U.S. Appl. No. 12/824,935.
Office Action dated Sep. 26, 2013 for U.S. Appl. No. 12/824,935.
Response dated Mar. 25, 2014 for U.S. Appl. No. 12/824,935.
Office Action dated Jun. 23, 2014 for U.S. Appl. No. 12/824,935.
International Search Report for PCT International Application No. PCT/CA20101000971 (Publication No. WO 2010148501), (2010).
International Preliminary Report on Patentability for PCT International Application No. PCT/CA2010/000971 (Publication No. WO 2010148501), (2010).
Guo et al., "Protein tolerance to random amino acid change," PNAS 101(25): 9205-9210, Jun. 22, 2004.
Matthews, "Structural and Genetic Analysis of Protein Stability," Annu. Rev. Biochem. 62:139-160, 1993.
Ng et al., "Predicting the Effects of Amino Acid Substitutions on Protein Function," Annu. Rev. Biochem. 7: 61-80, 2006.
Wan et al., "Epitope Map for a Growth Hormone Receptor Agonist Monoclonal Antibody, Mab 263," Molecular Endocrinology 17(11): 2240-2250, 2003.
International Search Report and Written Opinion issued by the International Searching Authority for Application No. PCT/US18/63289, dated Feb. 5, 2019, 14 pages.

* cited by examiner

A
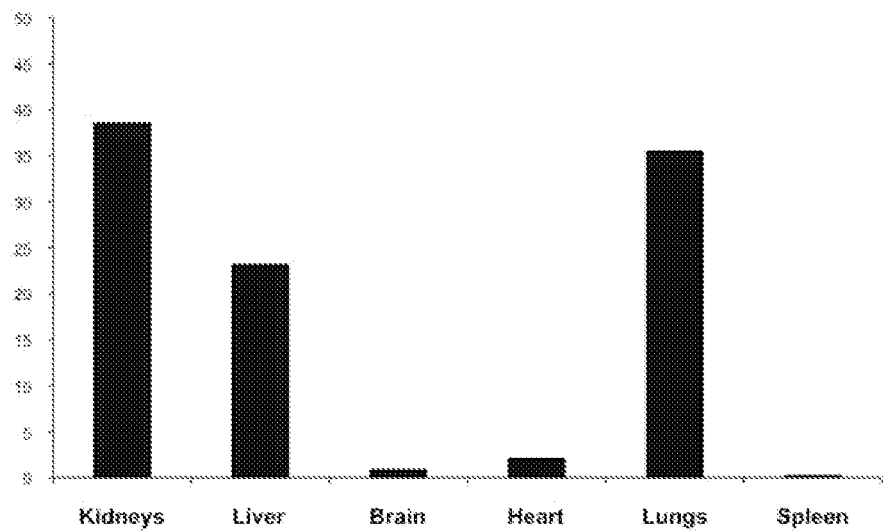
B
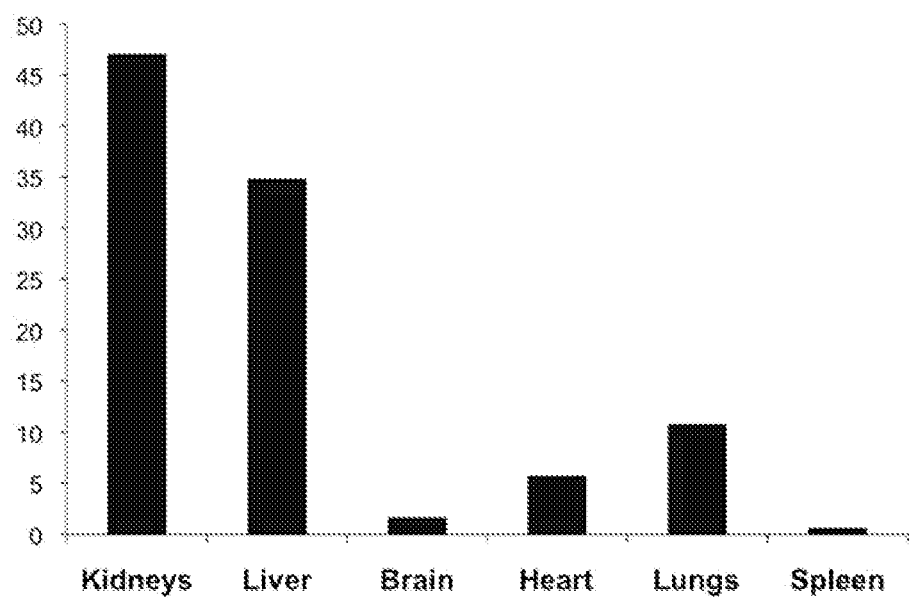
FIG. 4

| IHC Score | Intensity of Staining (Brief description) | Representative Image | Specimen Source (Ovarian tumour type and Grade) |
|---|---|---|---|
| - | No staining of tissue | | Normal ovarian tissue |
| -/+ | Very weak staining; Majority of cells negative for staining; weak staining of some cells | | Normal ovarian tissue |
| + | Weak staining of majority of cells | | Mucinous papillary adenocarcinoma Grade II-III |
| ++ | Light staining of majority of cells | | Serous papillary adenocarcinoma Grade II |
| +++ | Moderate staining of majority of cells | | Serous papillary adenocarcinoma Grade II |
| ++++ | Intense staining of majority of cells | | Serous papillary adenocarcinoma Grade II |

FIG. 17

Ovarian biopsy
Grade
Position (intensity ranking)

Normal ovarian tissue
H-7(-), H-8(-/+), H-10 (-)

Serous papillary adenocarcinoma
Grade I
D-5 (++), C-5(+), C-6 (+++)

Serous papillary adenocarcinoma
Grade II
G-5 (++), G8 (+++), G10 (+++)

Serous papillary adenocarcinoma
Grade III
E-3 (++++), F-4 (+++), F-7 (++++)

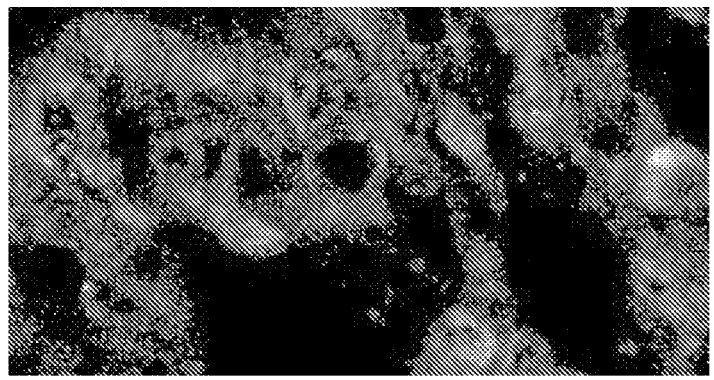
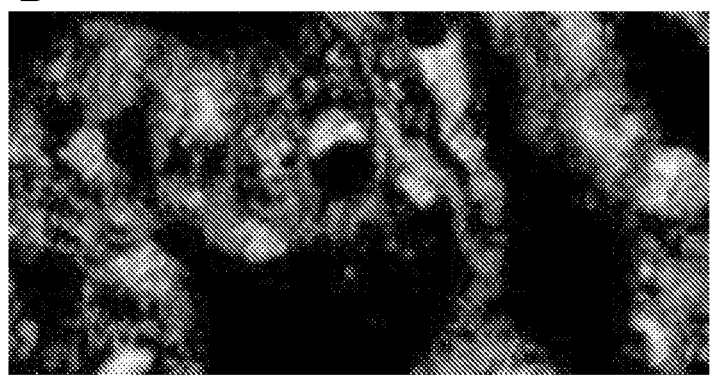
FIG. 20

A. SPIO Bead Control
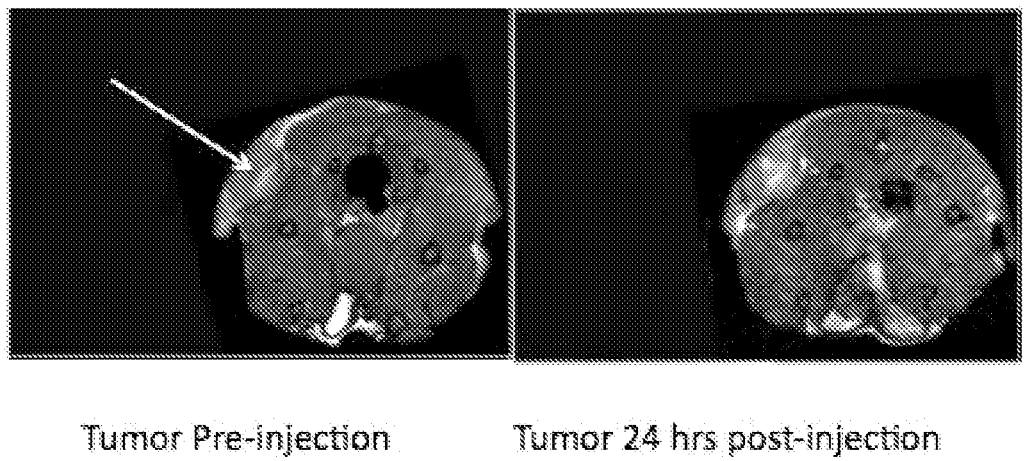
Tumor Pre-injection     Tumor 24 hrs post-injection
B. SPIO-SorC27 TRPV6-Binding Conjugate
Tumor Pre-injection     Tumor 24 hrs post-injection
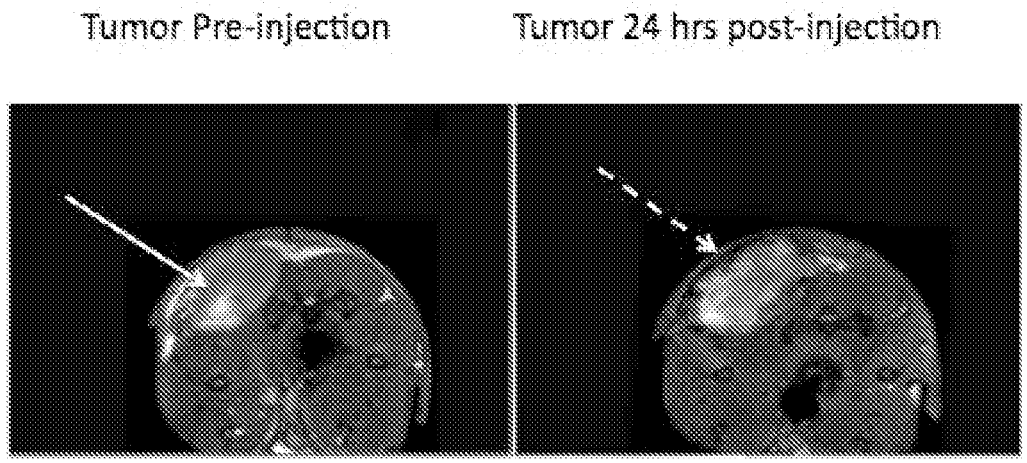
FIG. 23

Prostate

Breast

Ovarian

COMPOUNDS AND METHODS FOR THE DETECTION OF TRPV-6 CANCERS AND DRUG DELIVERY

CROSS REFERENCE TO RELATED APPLICATIONS

This application is a continuation of U.S. application Ser. No. 14/579,157, filed Dec. 22, 2014, now allowed, which is a continuation of U.S. application Ser. No. 12/824,935, filed Jun. 28, 2010, now abandoned, which claims priority to U.S. application No. 61/220,833 filed on Jun. 26, 2009 and to U.S. application No. 61/244,634 filed on Sep. 22, 2009, all of which are incorporated by reference herein in their entirety.

INCORPORATION OF SEQUENCE LISTING

A computer readable form of the Sequence Listing "SORI_001_04US_ST25.txt" (1 KB), submitted via EFS-WEB and created on Jul. 26, 2018, is herein incorporated by reference.

FIELD

The present invention relates to detection and diagnosis of Transient Receptor Potential Vanilloid 6 (TRPV6)-expressing cancers. Certain embodiments of the invention also relate to TRPV-6 binding compounds that target cells that express TRPV6 for use in diagnostics or drug delivery.

BACKGROUND

Soricidin (NCBI accession no. P0C2C6) is a fifty-four amino acid paralytic peptide isolated from the submaxilary saliva gland of the Northern Short-tailed Shrew (*Blarina brevicauda*). U.S. Pat. No. 7,119,168 (incorporated by reference herein in its entirety) describes soricidin, its paralytic activity and usefulness of the peptide for conditions, such as treating pain and neuromuscular disease. U.S. Pat. No. 7,273,850 (incorporated by reference herein in its entirety) describes that soricidin has paralytic activity, and among other things, provides data that it inhibits calcium uptake in two ovarian cancer cell lines.

One group of calcium ion channels implicated in cancer is the Transient Receptor Potential (TRP) channels that are found across the invertebrates and vertebrates. The Transient Receptor Potential Vanilloid (TRPV) members of the TRP super-family were named after it was discovered that they activate in the presence of vanilloids (capsaicin from hot peppers for example). The first four of these receptors tested (TRPV1, TRPV2, TRPV3 and TRPV4) all responded to capsaicin and were also responsible for detecting changes in temperature and other environmental signals. The remaining two of the TRPV sub-family, TRPV5 and TRPV6, were found predominantly in epithelial type or derived tissues and were responsible for influx of calcium ion into the cell. U.S. Pat. No. 7,205,108 describes genes encoding TRPV 8, 9 and 10 and their use as biomarkers for cancer and in associated diagnostic and therapeutic methods.

TRPV6 was identified as responsible for import of calcium into epithelial tissues of the intestine and hence uptake of calcium from the diet. These channels were also shown to be present in a number of other tissues in varying amounts, but most notably intestinal epithelial cell, kidney, placenta and pancreas. The expression of TRPV6 was measured as highly elevated in some cancer tissues and in some known ovarian, breast, prostate, and leukemia cancer cell-lines. (Peng et al. 2000; Zhuang et al. 2002).

Accordingly, there is a need for compounds and associated methods for detecting cells that express TRPV6. There is also a need for compositions and methods capable of targeting cells that express TRPV6 for the delivery of agents useful for the diagnosis or treatment of cancer.

SUMMARY

The present inventor has synthesized compounds that bind to TRPV6 calcium ion channels. These compounds have at least a portion that has sequence identity to a continuous string of amino acids from the C-terminal peptides of soricidin. In certain cases, the peptide component represents the entirety of the compound, while in other cases the peptide is a component of the compound, for example, if the compound comprises peptide conjugated to a drug or a detectable label.

It was not previously known that the structure of soricidin that provided calcium channel inhibition activity was separate from the structure that caused paralytic activity. Fluorescent conjugates of the compounds described herein bind to cells expressing TRPV6 protein in co-localization experiments with TRPV6 antibodies. TRPV6 has been shown to be overexpressed in a number of cancer-tissue samples and cell lines. TRPV6-binding compounds are useful for the identification of cancer as well as for targeting anti-cancer drug activity to cells that express TRPV. A further aspect includes the use of TRPV6 antibodies in the identification and diagnosis of cancer as well as for targeting anti-cancer drug activity to cells that express TRPV. In addition, fluorescently labeled TRPV6-binding compounds have been shown to be useful for imaging and identifying tumors in vivo. The TRPV6-binding peptides described herein have also been shown to be useful for targeting biomolecules to cells expressing TRPV6, such as tumor cells.

Accordingly, some embodiments include a compound comprising a Transient Receptor Potential Vanilloid 6 (TRPV6)-binding peptide conjugated to a biomolecule. Optionally, the compound may comprise all or part of a peptide with the amino acid sequence EGKLSSNDTEGGLCKEFLHPSKVDLPR (SEQ ID NO:1). In one embodiment, the compound comprises from 9 to 27 amino acids of SEQ ID NO:1. In one embodiment, the compound comprises a contiguous part of the C-terminal sequence of SEQ ID NO:1. In one embodiment, the compound comprises at least 9 contiguous amino acids of SEQ ID NO:1, at least 10 contiguous amino acids of SEQ ID NO:1 or greater than 10 contiguous amino acids of SEQ ID NO:1. In one embodiment, the compound comprises a TRPV6-binding peptide with at least 70%, at least 80%, or at least 90% identity to one of HPSKVDLPR, KEFLHPSKVDLPR or EGKLSSNDTEGGLCK-EFLHPSKVDLPR (SEQ ID NO:1). In some embodiments, the TRPV6-binding peptide comprises the amino acid sequence HPSKVDLPR or KEFLHPSKVDLPR.

In some embodiments, there is provided a compound comprising an antibody to TRPV6 conjugated to a biomolecule.

In one embodiment, the compound comprises a biomolecule with a detectable label. In some embodiments, the biomolecule is fluorescently, radioactively or immunologically labeled. In one embodiment, the detectable label comprises a magnetic resonance imaging (MRI) contrast agent. In one embodiment, the detectable label is superparamagnetic iron oxide (SPIO).

In one embodiment, the biomolecule is a therapeutic agent. Optionally, the therapeutic agent is an anti-cancer agent for example a taxane-based drug, anthracycline-type drug or a platin-based drug.

In some embodiments, the biomolecule is a small drug molecule, oligosaccharide, antibody, antibody epitope, nanometallic cluster, radioactively-labeled molecule, taxane-based drug, anthracycline-type drug, platin-based drug, antibiotic, anti-cancer drug, anti-fungal, anti-viral or anti-retroviral, or boron complex, epitope for an endogenous or therapeutically administered antibody, signaling peptide or oligosaccharide that recruits immune cells e.g. killer-T cells.

In one embodiment, the TRPV6-binding peptide and the biomolecule are attached through a spacer. In one embodiment, the TRPV6-binding peptide is conjugated to more than one biomolecule or to more than one type of biomolecule.

Also included are pharmaceutical compositions comprising a compound containing a TRPV6-binding peptide as described herein and a pharmaceutically acceptable carrier. Optionally, the pharmaceutical composition comprises a TRPV6-binding peptide conjugated to a biomolecule, or to a plurality of biomolecules.

One embodiment includes a method for detecting TRPV6 protein in a sample comprising contacting the sample with a TRP-binding peptide comprising all or part of a peptide comprising EGKLSSNDTEGGLCKEFLHPSKVDLPR (SEQ ID NO:1) and detecting the TRPV6-binding peptide. In one embodiment, the TRPV6-binding peptide is detected using an antibody that selectively binds the TRPV6-binding peptide.

Another embodiment includes a method for detecting TRPV6 protein in a sample comprising contacting the sample with a compound comprising a TRPV6-binding peptide conjugated to a biomolecule and then detecting the biomolecule. For example, in one embodiment the biomolecule is a fluorophore and the compound comprising the TRPV6-binding peptide is detected by detecting the fluorophore.

A further embodiment includes the use of the compounds described herein for detecting TRPV6 in a sample. In one embodiment, the sample is a bodily fluid such as blood, saliva or urine.

Some embodiments relate to methods for identifying cancer in a sample from a subject comprising detecting TRPV6 mRNA or protein in the sample and comparing the amount of TRPV6 mRNA or protein in the sample with a control sample, wherein an increased amount of TRPV6 mRNA or protein in the sample compared to the control is indicative of cancer. In one embodiment, the sample is a bodily fluid. In some embodiments, the TRPV6 protein is detected in vivo, ex vivo or in vitro. The TRPV6 protein can be detected using the compounds described herein or antibodies directed to TRPV6. In some embodiments, TRPV6 mRNA is detected using PCR, RT-PCR or real time quantitative RT-PCR. In some embodiments, said cancer is an early stage cancer such as stage I or stage II cancer.

In some embodiments the subject can be a mammal, such as a human. The sample may comprise a bodily fluid, excreta, tissue sample, tumor sample or microvesicles. In one embodiment, the bodily fluid is blood, urine, saliva, plasma, cerebrospinal fluid, mucus, vaginal secretions, lymph or pleural fluid.

In some embodiments the methods described herein are used to identify breast cancer, ovarian cancer, blood cancer, brain cancer, retinal cancer, liver cancer, thyroid cancer, colon cancer, prostate cancer, pancreatic cancer, glial cancer, leukemia or endometrial cancer. In one embodiment, the cancer is metastatic cancer or lymph node metastatic cancer.

In one embodiment, the methods described herein are used to stage cancer. In some embodiments, the method includes comparing the amount of TRPV6 mRNA or protein in a sample with a control sample or samples that have stage I, II, III or IV cancer.

In another embodiment, the methods described herein are used to grade cancer cells or tumors. In some embodiments, the cancer is ovarian cancer. In one, the methods disclosed herein identify subjects with grade I ovarian cancer.

A further embodiment includes a method of manufacturing one of the compounds disclosed herein comprising conjugating a biomolecule to a TRPV6-binding peptide or to a TRPV6 antibody. In one embodiment, the TRPV6-binding peptide is covalently conjugated to a biomolecule. For example, in one embodiment the TRPV6-binding peptide comprises all or part of SEQ ID NO:1 and the biomolecule is attached through the cystein thiol corresponding to position 14 in SEQ ID NO:1. In one embodiment, the biomolecule is conjugated to the peptide through an activated maleimide.

Yet another embodiment includes a method of delivering a biomolecule to a cell expressing TRPV6 comprising contacting the cell with a compound comprising a TRPV6-binding peptide conjugated to a biomolecule or a TRPV6 antibody conjugated to a biomolecule. In one embodiment, the biomolecule comprises a detectable label or a therapeutic agent. The step of contacting the cell with the compound can occur in vivo, in vitro or ex vivo. In some embodiments the cell expressing TRPV6 comprises a tissue, tumor or microvesicle.

Additional embodiments include kits for detecting TRPV6 in a sample comprising reagents for conducting the methods described herein and instructions for use. Other embodiments include kits for diagnosing cancer, reagents for conducting the methods described herein and instructions for use.

In another aspect, there is provided a method of identifying a cancer tumor in a subject. In one embodiment, the cancer tumor over-expresses TRPV6. In some embodiments, the method comprises administering to the subject a compound comprising a TRPV6-binding peptide or an antibody to TRPV6 as described herein. The TRPV6-binding peptide or antibody to TRPV6 is then detected, indicating the presence of TRPV6. In one embodiment, the TRPV6-binding peptide is detected by detecting a biomolecule conjugated to the peptide. Optionally, regions of the subject with increased levels of TRPV6 are then identified, wherein increased levels of TRPV6 are indicative of a tumor. In one embodiment, the levels TRPV6 are compared to a control level such as those observed in a non-cancerous tissue, a pre-determined control level, or an average level taken throughout the subject. In one embodiment, TRPV6 is detected in vivo, for example by detecting a fluorescent label conjugated to the TRPV6-binding peptide or antibody to TRPV6. In one embodiment, TRPV6 is detected using magnetic resonance imaging (MRI) and an MRI contrast agent conjugated to a TRPV6-binding peptide. In some embodiments, the cancer tumor is a prostate tumor, a breast tumor or an ovarian tumor.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the invention will now be described in relation to the drawings in which:

FIG. 4 shows the distribution of SorC13-Cy5.5 compound in CD1 mice after i.v. injection over time after perfusion to wash out fluids. The Y-axis is the percentage of total fluorescence measured in all tissues. The highest percent uptake (of total fluorescence) of SorC13-Cy5.5 compound was observed in liver, lung and kidney. Lymph node is not shown because perfusion washes out lymph. Panel A shows the distribution 4 hours after i.v. injection and Panel B 24 hours after i.v. injection.

FIG. 6B shows cells imaged with green TRPV-antibody while FIG. 6C shows the same field of cells imaged with red SorC27-cy5.5.

FIG. 6D shows both images superimposed and the co-localization of TRPV6 and SorC27-cy5.5 in cells transfected with TRPV6 vector.

PCR of cDNA library from PC-3 cells; Lane 3: blank; Lane 4: MW ladder; Lane 5: blank.

Figure 14:
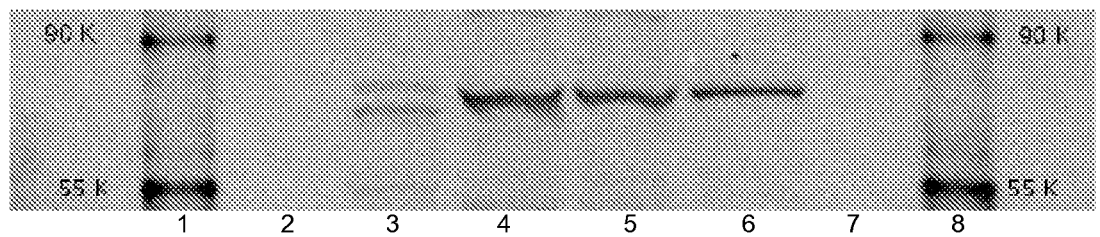

FIG. 14 is a Western blot showing the detection of TRPV6 protein over-expression in extracts from human ovarian, breast and prostate cancer cell lines. Lane 1: Molecular weight standard; 2: blank; 3: HEP G2 (positive control); 4: Breast cancer cell line T 47D; 5: Ovarian cancer cell line SKOV-3; 6: Prostate cancer cell line PC-3. In lane 3, the HEP G2 (hepatoblastoma) lysate shows two bands: the top band is TRPV6 that has not been glycosylated while the fully glycosylated TRPV6 is shown in the second band. The de-glycosylated TRPV6 is heavily produced in all three cancer cell types. De-glycosylation of membrane-bound TRPV6 has been shown to trap the ion channel in the membrane and to increase channel activity (Lu et al., 2008).

Figure 15A:
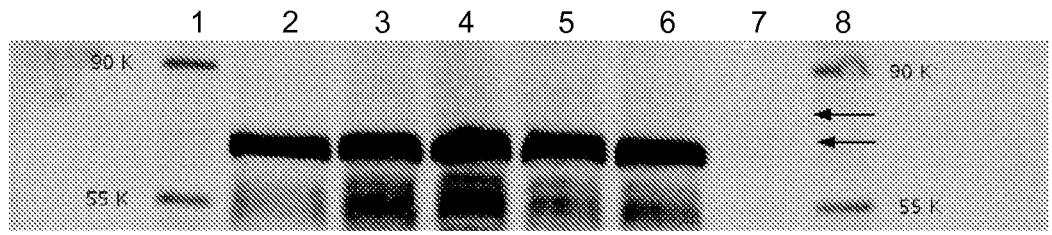
Figure 15B:
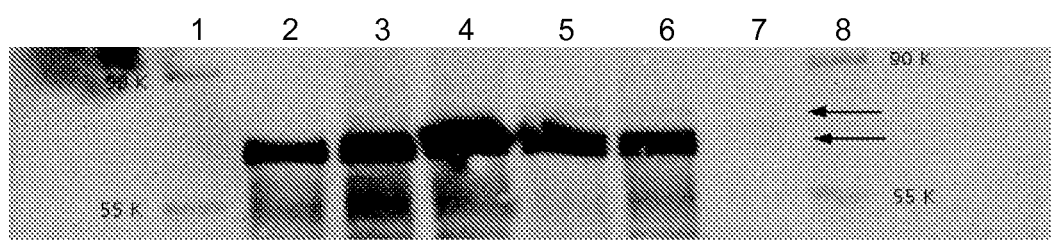
Figure 15C:
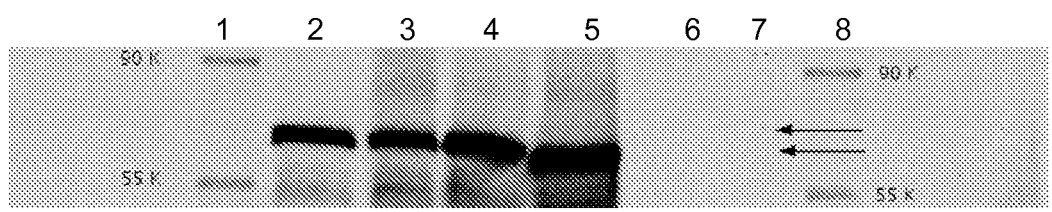
Figure 15D:
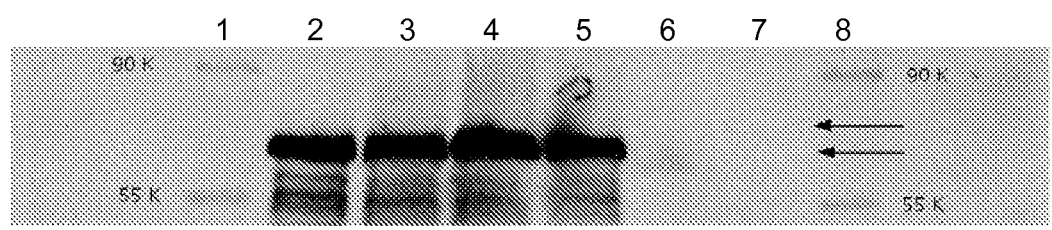

FIGS. 15A, 15B, 15C and 15D are Western blots showing the detection of TRPV6 protein in extracts from 18 human ovarian tumor samples. Each separate patient/tumour is cited as an alphanumeric code. In all sections the top arrow at the right of the image indicates the position of the glycosylated form of TRPV6 while the lower arrow indicates the position of the de-glycosylated form of TRPV6 protein. FIG. 15A: Lane 1: molecular weight standard; 2: LTL-175; 3: LTL-205; 4: LTL-234; 5: LTL-237; 6: LTL-246; 7: HEP G2 (positive control); 8: molecular weight standard. FIG. 15B: Lane 1: molecular weight standard; 2: LTL-247; 3: LTL-258; 4: LTL-259; 5: LTL-260; 6: LTL-269; 7: HEP G2 (positive control); 8: molecular weight standard. FIG. 15C: Lane 1: molecular weight standard; 2: LTL-273; 3: LTL-284; 4: LTL-290; 5: LTL-300; 6: PC-3; 7: blank; 8: molecular weight standard. FIG. 15D: Lane 1: molecular weight standard; 2: LTL-305; 3: LTL-315; 4: LTL-317; 5: LTL-320; 6: PC-3; 7: blank 8: molecular weight standard. The PC-3 was a small protein load (50 ug) to match the ovarian tumor biopsy protein load (50 ug) and shows a very weak signal, barely visible in 15D (for example see FIG. 14, lane 3 for HEP G2 and lane 6 for PC-3). Trapped, deglycosylated TRPV6 is the predominant form observed in each ovarian tumor sample tested. The bands in the HEP-G2 control are very faint with this amount of loaded protein and indicate further the over-expression of TRPV6 in the tested biopsies.

Figure 16:
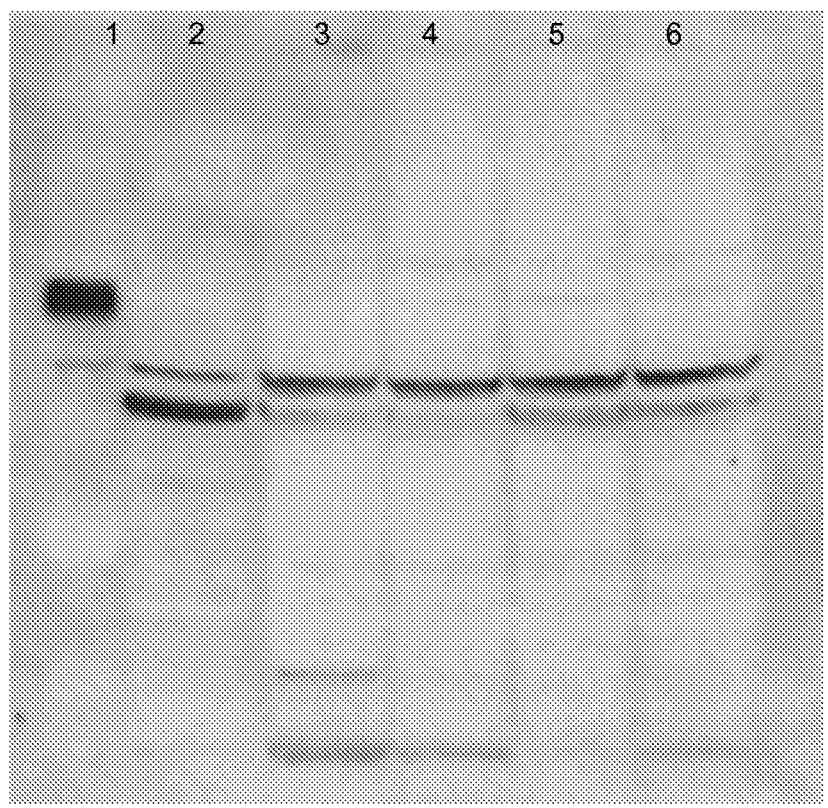

FIG. 16 is a Western blot showing the detection of TRPV6 protein over-expressed in extracts of human glioblastoma (U87MG), human colon (CaCo-2) and pancreatic carcinoma cells (Panc1). Lane 1: Molecular weight markers with the light thin band at 75 kDa; 2: U87MG cells; 3: CaCo-2 cells; 4: Panc1 cells at 2 culture passages; 5: Panc1 cells at 5 culture passages; 6: Panc1 cells at 7 culture passages. In the last three lanes, increasing the passage number appears to increase the amount of de-glycosylated TRPV6. The top band is the glycosylated form of the ion channel and the lower band is the de-glycosylated form of TRPV6.

FIG. 17 shows the calibration of grading for tissue microarray immunohistochemical (IHC) scores with corresponding representative sample images.

Figure 18:
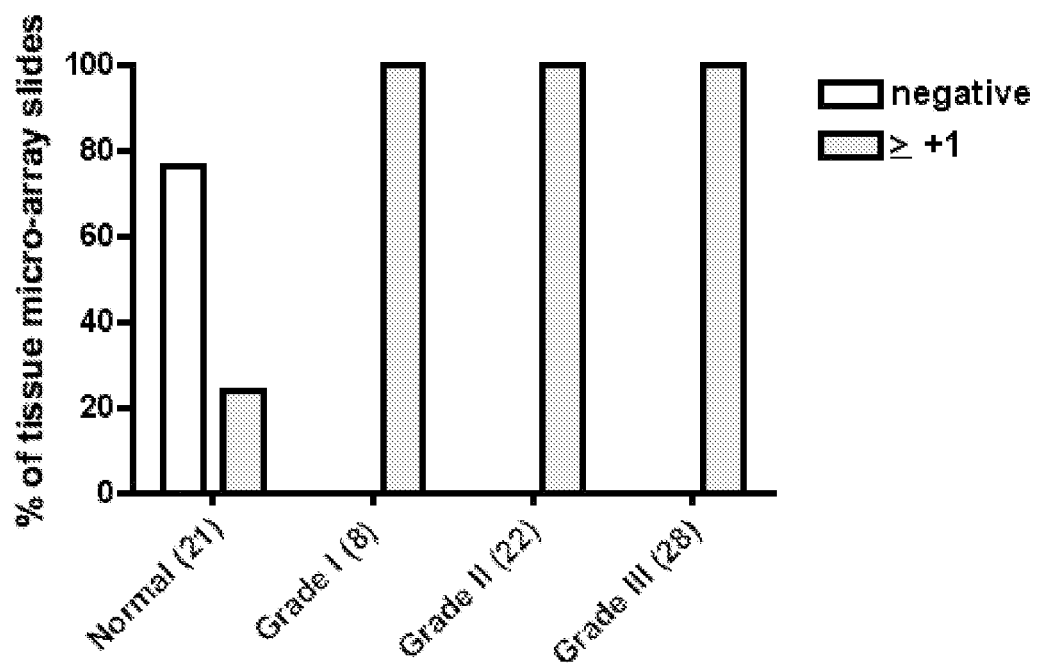

FIG. 18 shows the percentage of tissue micro-array slides that were negative for TRPV6 antibody staining or had a stain intensity score ≥1 for normal ovarian tissue samples compared to serous papillary adenocarcinoma tissue samples with grade I, grade II, or grade III cancer. 100% of serous papillary adenocarcinoma tissue samples had a stain intensity score of ≥1, compared with only about 24% of normal ovarian tissues.

Figure 19:
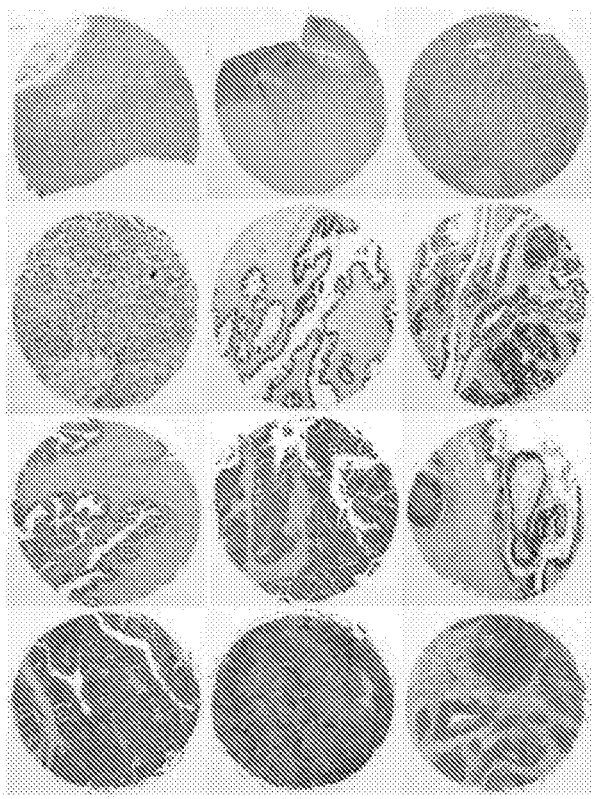

FIG. 19 shows the immunohistochemical detection of TRPV6 in micro-array samples of normal ovarian tissues, as well as in samples of Grades I, II and III serous papillary carcinoma. TRPV6-antibody staining intensity scores (−, −/+, +, ++, +++ or ++++) are also given for each sample.

FIG. 20 shows the co-localization of antibodies to TRPV6 and fluorescently labeled SorC27-cy5.5 in a tissue microarray sample of grade II serous papillary adenocarcinoma. Panel A shows an ovarian tumour biopsy stained with an antibody to TRPV6 while Panel B shows the same sample stained with the fluorescent tagged peptide SOR-C27-cy5.5.

Figure 21:
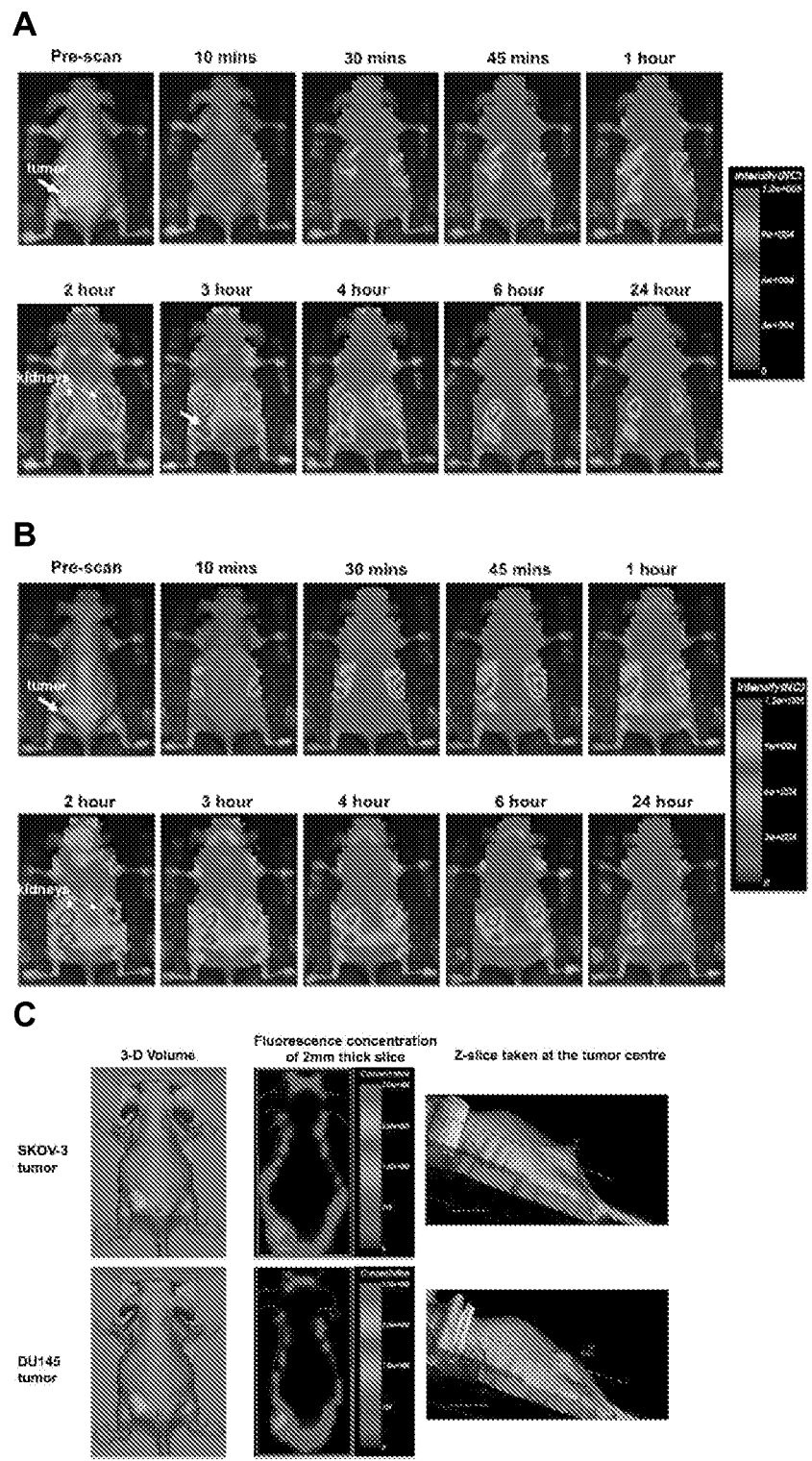

FIG. 21 shows the time dependent localization of SorC27-cy5.5 in xenograft mouse models of ovarian (FIG. 21A) and prostate (FIG. 21B) cancer tumors. FIG. 21C shows: 3-D image of a mouse indicating the plane of observation (left), an image of a 2 mm slice of the mice through the center (middle) and, an image showing a perpendicular 'slice' through the center of the tumors (right) for both ovarian (SKOV-3; top) and prostate (DU145; bottom) tumors.

Figure 22A:
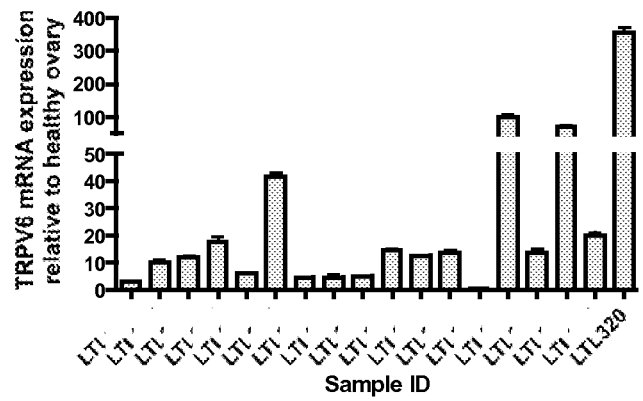
Figure 22B:
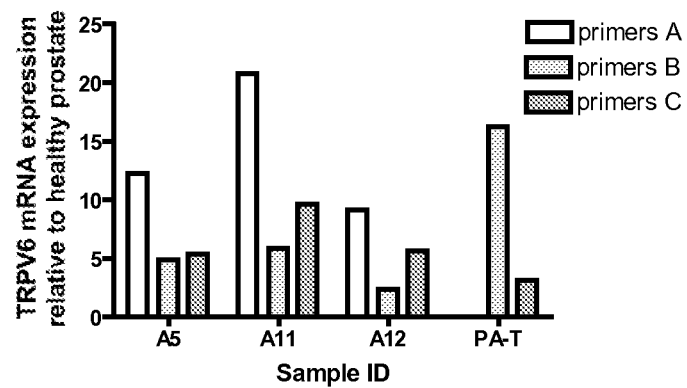
Figure 22C:
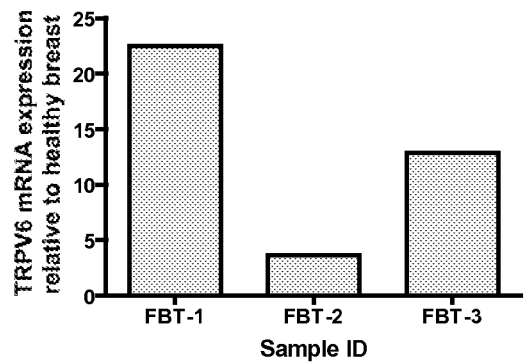

FIG. 22 shows TRPV6 mRNA expression relative to healthy controls in samples of ovarian (A), prostate (B) and breast (C) cancer.

FIG. 23 shows the localization of an MRI enhancement agent conjugated to the TRPV6 binding peptide SorC27 (SPIO-SorC27) to SKOV-3 derived ovarian tumors xenografted into CD-1 nude mice. Panel A shows the tumor indicated by the white arrow prior to and 24 hours after injection of SPIO control beads. Panel B shows the tumor prior to (white arrow) and 24 hours after injection with SPIO-SorC27 and the localization of the contrast agent to the tumor site (dashed white arrow).

Figure 24A:
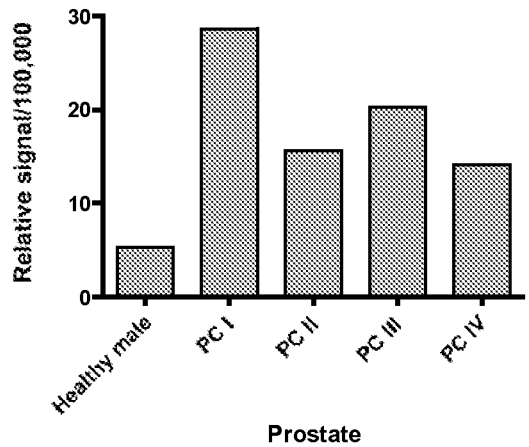
Figure 24B:
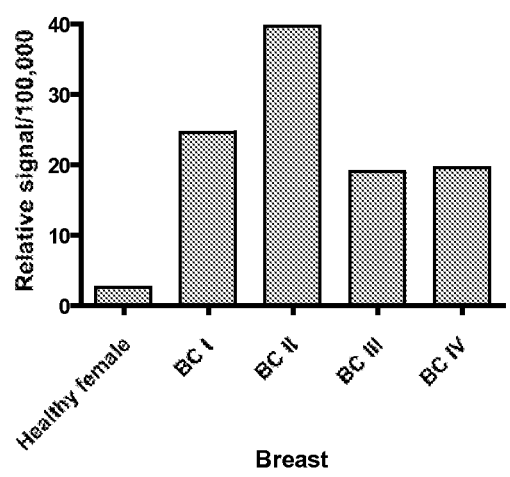

FIG. 24 shows RT-PCR analysis of the amount of TRPV6 mRNA isolated from blood samples from healthy controls and patients with prostate (FIG. 24A), breast (FIG. 24B) and ovarian (24C) cancers at different cancer stages. RT-PCR of TRPV6 mRNA easily distinguishes subjects with stage I cancer from healthy controls.

Figure 25:
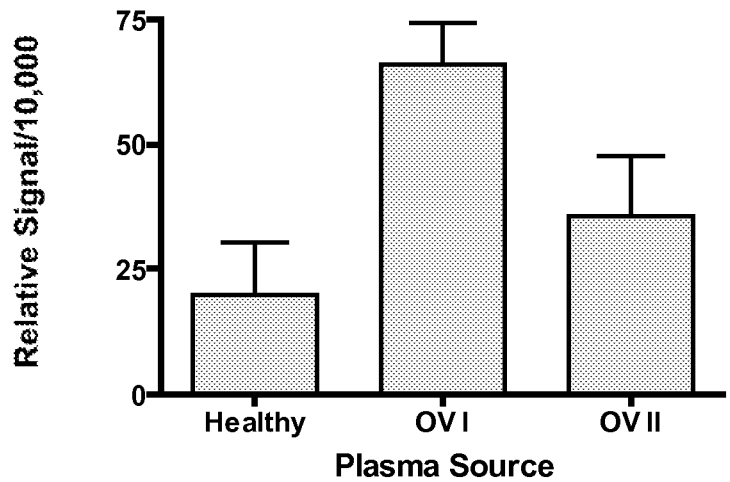

FIG. 25 shows the amount TRPV6 mRNA determined by RT-PCR in blood plasma of healthy women compared to women with either Stage I or Stage II ovarian cancer. The data represent the integrated band density readings of the amplicons from the samples. The samples were determined in triplicate for each sample. Both Stage I ($p<0.0001$) and Stage II ($p=0.047$) TRPV6 levels were statistically significantly larger than observed in plasma from healthy women.

Figure 26A:
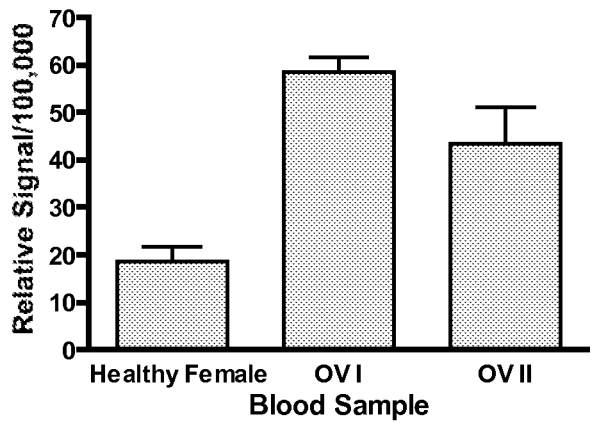
Figure 26B:
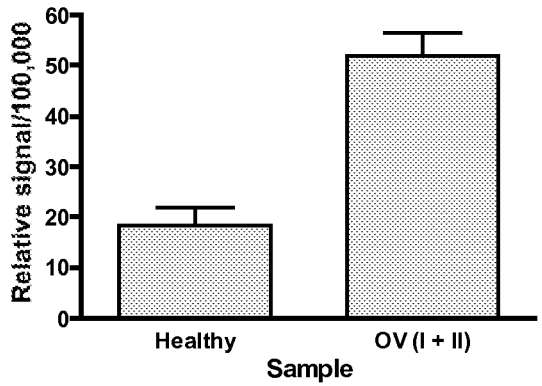

FIG. 26A shows Western blot data for TRPV6 protein levels in samples of blood plasma from healthy women compared to women with Stage I and Stage II ovarian cancer. The figure shows the quantified band density of TRPV6 antibody staining. Both Stage I ($p=0.0001$) and Stage II ($p=0.0210$) TRPV6 levels were significantly higher than those observed in plasma from healthy women. FIG. 26B compares the band density from Western Blots of healthy plasma and combined Stage I and II data ('early stage' ovarian cancer). The plasma from combined stage I and II cancer patients contained statistically significant higher amounts of TRPV6 protein than healthy women ($p=0.0006$).

DETAILED DESCRIPTION

The inventor has determined that TRPV6 calcium channel expression is upregulated in certain cells, such as ovarian cancer cells, and that this overexpression is indicative of cancer. The present description provides new methods for detecting TRPV6 overexpression for identifying and/or diagnosing cancer. The application also provides new compounds and methods that target TRPV6 protein or cells that express TRPV6 such as cancer cells.

In one embodiment, the inventor synthesized compounds that bind to calcium channels and in particular to TRPV6 calcium channels. The TRPV6-binding compounds described herein have sequence identity to part of soricidin but do not exhibit paralytic activity. It is surprising that the compounds retain TRPV-6 binding activity in the absence of paralytic activity. It was not previously known that soricidin has two functional domains in its structure, one portion that binds to calcium channels and the other portion which binds to sodium channels. It was also unknown that peptides could be prepared that separated the calcium channel detection/binding activity from the sodium-channel binding paralytic activity.

The inventor has determined that it is an N-terminal domain of soricidin that has the paralytic function and a C-terminal domain that has the calcium channel inhibitor function, and more specifically TRPV6-binding activity. Truncating soricidin at the N-terminal successfully produced peptides that retain calcium channel binding/detection activity without exhibiting paralytic activity. The compounds therefore are more likely to bind to TRPV6 in vivo because sodium channels cannot bind the compounds and remove them from circulation. As well, the calcium channel-binding activity is now obtained without the unwanted side effect of sodium channel-binding, which avoids paralysis and other potential side effects. The surprising nature of the embodiments described herein is emphasized by considering that, while bifunctional large proteins and enzymes are common in biological systems, inherent bifunctionality is a very rare phenomenon in small peptides, particularly where one end of the peptide binds calcium channels and the other end of the peptide binds sodium channels. Reports in the literature of bifunctionality have typically resulted from artificial production, for example, where two different peptides have been chemically fused (Anes et al. 2006; Yamamoto et al. 2008).

The compounds described herein typically have a peptide component that is half the length of soricidin, or shorter. In one embodiment, the peptide retains TRPV6 binding activity. In some embodiments, the peptide component is the entirety of the compound, while in other embodiments it is a component of the compound, for example, if the compound comprises peptide conjugated to a drug or a detectable label. In one embodiment, the TRPV6-binding peptide comprises all or part of a peptide comprising EGKLSSNDTEGGLCKEFLHPSKVDLPR (called "SorC27"; SEQ ID NO:1). The TRPV6-binding peptide optionally comprises a contiguous part of SEQ ID NO:1. In some embodiments, the TRPV6-binding peptide comprises a contiguous part of the C-terminal sequence of SEQ ID NO:1. Optionally the TRPV6-binding peptide comprises at least: 9, 10, 11, 12, 13, 14, 15, 16, 17, 18, 19 or 20 amino acids of SEQ ID NO:1. In some embodiments, the compound comprises a TRPV6-binding peptide that has at least 50% identity over its full length to a part of SEQ ID NO:1. In some embodiments, the compound comprises a TRPV6-binding peptide that has at least 70%, 80% or 90% identity over its full length to a part of SEQ ID NO:1. In some embodiments, the TRPV6-binding peptide optionally comprises, consists essentially of or consists of the amino acid sequence: HPSKVDLPR (called "SorC9"; amino acid nos. 19-27 of SEQ ID NO:1), KEFLHPSKVDLPR (called "SorC13"; amino acid nos. 15-27 of SEQ ID NO:1) or EGKLSSNDTEGGLCKEFLHPSKVDLPR ("SorC27"; SEQ ID NO:1). The SorC9 9 amino acid sequence HPSKVDLPR contains three positive charges at physiological pH that are expected to interact with the four negatively charged aspartic acids that are present at the entrance to the calcium channel of the TRPV6 tetramer (den Dekker et al. 2003).

In some embodiments, the TRPV6-binding peptides are typically 35 or 30 amino acids or less, optionally less than: 27, 25, 20, 15 or 13 amino acids long, while optionally at least 9 amino acids long. The TRPV6-binding peptide optionally comprises at least 9-13, 10-15, 15-20, 20-25 or 20-27 amino acids. In some embodiments, amino acids may be added to the TRPV6-binding peptides described herein. One can readily make longer peptides by adding a variety of additional amino acids to the SorC27 sequence to make a TRPV6-binding peptide that could be up to, for example, 30, 35, 40 or 45 amino acids long (e.g. additional amino acids corresponding to the soricidin amino acid sequence such as one or more of the amino acids that are immediately towards the N-terminal segment of SorC27 in soricidin (SILARPAELNTETCILEC SEQ ID NO:2), a targeting sequence, or other amino acids) or longer.

In some embodiments, the compounds comprise TRPV6-binding peptide conjugated to a biomolecule, which is optionally a second protein or peptide, either directly or through a spacer. In some embodiments, the spacer molecule may be a carbon containing substance. For example, the spacer may be a short peptide, such as 3 amino acids (Gly-Gly-Gly) or longer, or a carbon chain, for example, $(CH_2)_n$ wherein n optionally equals 1 to 5, 1 to 10, or greater than 10. In other embodiments the spacer is optionally a polymer, for example Poly-ethylene Glycol (PEG), a sugar, a lipid or the like.

As noted above, a TRPV6-binding peptide of the invention will have calcium channel binding activity. The peptides having such activity are readily identified with any known assays suitable for measuring binding of the peptides with TRPV6. For example, in one embodiment, a peptide having calcium channel inhibition activity is optionally identified by determining that the peptide reduces calcium channel activity by reducing (i.e., partially or fully inhibiting) the flow of calcium through calcium channels. TRPV6-binding activity can also be measured using methods such as: internalized calcifluors (such as FURA-2am); whole cell patch clamping to measure inhibition calcium currents electrophysiologically; equilibrium binding assays using peptides labeled with detectable tags such as radioactive or fluorescent tags; and/or NMR determination of 'bound' and 'unbound' peptides. In some embodiments, the TRPV6-binding peptides also have i) calcium channel blocking and ii) lack of paralytic activity.

Calcium channel binding activity is optionally identified by using a readily available cell line (e.g. human embryonic kidney cell lines-HEK293) transfected with an expression vector for TRPV6. Such transfected cells are readily aliquoted and stored (typically −80° C.) until required. This provides a standard transfected cell preparation to test for detection of calcium ion channels in the cells and for testing for the inhibition of these ion channel activities. Optionally the peptides have an equilibrium inhibition constant of less than: 1000 nM, 150 nM or 100 nM in LNCaP, HEK293 or SKOV-3 cell models. For example, the equilibrium dissociation constant (Kd) for SorC27 is 140 nM and for SorC13 is 100 nM in an LNCaP model. Based on a linear relationship with the number of amino acids, the Kd of SorC9 is expected to be approximately 90 nM.

The TRPV6-binding peptides described herein optionally include analogs of the aforementioned peptides. Analogs of the protein of the invention optionally include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the peptides of the invention with amino acids of similar charge, size, and/or hydrophobicity characteristics. When only conserved substitutions are made, the resulting analog should be functionally equivalent. Non-conserved substitutions involve replacing one or more amino acids of the amino acid sequence with one or more amino acids that possess dissimilar charge, size, and/or hydrophobicity characteristics. The analog is optionally a peptoid, which is an N-substituted polyglycine with amino acid R groups attached at the N atom. Another analog is optionally a peptide synthesized from D-amino acids rather than the natural L-amino acids.

One or more amino acid insertions are optionally introduced into the TRPV6-binding peptide sequences of the invention. Amino acid insertions consist of single amino acid residues or sequential amino acids ranging for example from 2 to 15 amino acids in length.

Deletions consist of the removal of one or more amino acids, or discrete portions from the amino acid sequence of the peptide. The deleted amino acids may or may not be contiguous.

Analogs of a TRPV6-binding peptide of the invention are optionally prepared by introducing mutations in a nucleotide sequence encoding the peptide. Mutations in nucleotide sequences constructed for expression of analogs of a protein of the invention preserve the reading frame of the coding sequences. Furthermore, the mutations will preferably not create complementary regions that could hybridize to produce secondary mRNA structures such as loops or hairpins, which could adversely affect translation of the mRNA.

Mutations are optionally introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures are employed to provide an altered gene having particular codons altered according to the substitution, deletion, or insertion required. Deletion or truncation of a peptide of the invention is also readily achieved by utilizing convenient restriction endonuclease sites adjacent to the desired deletion. Subsequent to restriction, overhangs may be filled in, and the DNA re-ligated. Exemplary methods of making the alterations set forth above are disclosed by Sambrook et al. (Sambrook J et al. 2000. Molecular Cloning: A Laboratory Manual (Third Edition), Cold Spring Harbor Laboratory Press).

In addition, analogs of a TRPV6-binding peptide of the invention are readily prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). The TRPV6-binding peptides of the invention also include peptides having sequence identity to a peptide of the invention, mutated peptides and/or truncations thereof as described herein. Such peptides have amino acid sequences that correspond to nucleic acid sequences that hybridize under stringent hybridization conditions (see discussion of stringent hybridization conditions herein) with a probe used to obtain a peptide of the invention. Peptides having sequence identity will often have the regions that are characteristic of the protein.

Other useful peptides of the invention optionally comprise, consist essentially of or consist of an amino acid sequence with at least: 30%, 40%, 50%, 60%, 70%, 80%, 90% or 95% sequence identity to all or part of SEQ ID NO:1 described herein, wherein the peptide has TRPV6-binding activity. Sequence identity is typically assessed by the BLAST version 2.1 program-advanced search (parameters as above; Altschul, S. F., Gish, W., Miller, W., Myers, E. W. & Lipman, D. J. (1990) "Basic local alignment search tool." J. Mol. Biol. 215:403-410). BLAST is a series of programs that are available online through the U.S. National Center for Biotechnology Information National Library of Medicine Building 38A Bethesda, Md. 20894) The advanced B last search is set to default parameters. References for the Blast Programs include: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); Zhang, J. & Madden, T. L. (1997) "PowerBLAST: A new network BLAST application for interactive or automated sequence analysis and annotation." Genome Res. 7:649-656). In a further embodiment, there is provided a compound comprising an antibody to TRPV6 conjugated to a biomolecule.

Preparation of Antibodies

In one aspect, antibodies to TRPV6 are useful in accordance with the embodiments described herein. In another aspect, antibodies to the TRPV6-binding peptides, or antibodies to the compounds comprising the TRPV6-binding peptides, are useful to identify the presence of the peptide in a test sample. Any method of labeling the antibody that would report on peptide density/location would be useful (e.g. radioactively labeled peptide or fluorescently tagged peptide). The antibody is typically a monoclonal antibody or a polyclonal antibody. The antibodies are also valuable for immuno-purification of peptides. For example, one may contact a biological sample with the antibody under conditions allowing the formation of an immunological complex between the antibody and a peptide recognized by the antibody and detecting the presence or absence of the immunological complex whereby the presence of the peptide of the invention is detected in the sample. The invention also includes compositions preferably including the antibody, a medium suitable for the formation of an immunological complex between the antibody and a peptide recognized by the antibody and a reagent capable of detecting the immunological complex to ascertain the presence of TRPV6, the TRPV6-binding peptides of the invention or similar peptides.

To recognize the TRPV6-binding peptides of the invention, one may generate antibodies against a range of unique epitopes throughout the peptides. Optionally, to recognize the compounds comprising the TRPV6-binding peptides one may generate antibodies against a range of unique epitopes throughout the compound.

Monoclonal and polyclonal antibodies are prepared according to the description in this application and techniques known in the art. For examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705 that are incorporated by reference in their entirety. Examples of the preparation and uses of polyclonal antibodies are disclosed in U.S. Pat. Nos. 5,512,282, 4,828,985, 5,225,331 and 5,124,147, which are incorporated by reference in their entirety.

The term "antibody" as used herein includes fragments thereof which also specifically react with TRPV6 or a TRPV6-binding peptide of the invention. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

In one embodiment, a TRPV6 protein may be detected in a sample by contacting the sample with a TRPV6-binding peptides and then detecting the TRPV6-binding peptide with an antibody that selectively binds the TRPV6-binding peptide. In some embodiments the antibody selectively binds a TRPV6-binding peptide or compound of the invention but does not bind soricidin.

Compounds of TRPV6-Binding Peptide Conjugated to a Biomolecule

The embodiments described herein include novel compounds comprising a TRPV6-binding peptide conjugated to a biomolecule. As used herein, a "biomolecule" includes any atom or molecule that is detectable through chemical, biological or physical means or exhibits chemical or biological activity. In some embodiments, the "biomolecule" comprises an inorganic molecule such as boron clusters and iron, gold, silver and nickel nano-structures. In one embodiment, the biomolecule comprises a detectable label or a therapeutic agent. In one embodiment, the biomolecule is a moiety of the compound that is distinguishable from the TRPV6-binding component of the compound.

As used herein, "conjugated to a biomolecule" refers to linking the TRPV6-binding peptide with a biomolecule. In some embodiments, the linking is the result of a chemical bond between a TRPV6-binding peptide and a biomolecule. In one embodiment, the linking is a covalent bond. The TRPV6-binding peptide may also be conjugated to a biomolecule through the use of recombinant genetic technologies wherein a nucleic acid sequence encodes both the TRPV6-binding peptide and a protein biomolecule. In some embodiments, the TRPV6-binding molecule is directly linked to a biomolecule. In other embodiments, a spacer is used to link the TRPV6-binding peptide with the biomolecule. In some embodiments, a TRPV6-binding molecule may also be chemically modified such that it comprises a biomolecule, such as by radioactively labeling the TRPV6-binding peptide. In one embodiment the biomolecule is conjugated to the TRPV6-binding peptide through a bond that can be hydrolyzed by general hydrolytic enzymes.

The compounds and compositions described herein may be used to detect or bind TRPV6 protein in vivo, in vitro or ex vivo. In some embodiments, the compounds include a biomolecule that comprises a detectable label. Any suitable biomolecular labeling system known in the art may be used to detectably label the TRPV6-binding peptides described herein. In some embodiments, the label is selected from the group consisting of a radioisotope, a bioluminescent compound, a chemiluminescent compound, a fluorescent compound, a metal chelate, and an enzyme. In some embodiments, the biomolecule may comprise a fluorescent, radioactive or immunological labeled. As used herein the terms "fluorescent label" or "fluorophore" refer to a molecule or moiety that can absorb energy of a specific wavelength and re-emit energy at a different specific wavelength. For instance, examples of fluorescent labels include, but are not limited to, Cy2, FluorX, Cy3, Cy3.5, Cy5, Cy5.5, Cy7, fluorescein isothiocyanate (FITC), Texas Red, or Rhodamine. In some embodiments, the compound includes more than one biomolecule conjugated to TRPV6-binding peptides.

The compounds described herein can be used to deliver diagnostically or therapeutically useful biomolecules to tumors, tissues or cells that produce TRPV6. In some embodiments the compound includes a biomolecule that is detectable by Positron Emission Tomography (PET), radiometric detection, or by Magnetic Resonance Imaging (MRI).

In one embodiment, the biomolecules conjugated to the TRPV6-binding peptides include metallic nano-clusters. In some embodiments, metallic clusters such as SPIO (super paramagnetic iron oxide) provide for very sensitive detection using MRI (Magnetic Resonance Imaging) that could be used for primary detection of TRPV6-rich tumors, tissues and cells. As shown in Example 28 and FIG. 23, the TRPV6-binding peptide SorC27 conjugated to SPIO targets tumors and can be used to identify cancer tumors in vivo.

In some embodiments, the compounds and methods described herein allow for the estimation of tumor volume or for following the change in tumor volume during the course of treatment of the cancer. Microvesicles sloughed of from TRPV6-rich tumors and present in a bodily fluid are also readily detected by metallo-TRPV6-binding peptide conjugates.

In another embodiment, the TRPV6-binding peptides are conjugated with biomolecules that are radio-molecules such as $^{18}$F-containing biomolecules. These compounds target TRPV6-expressing tumors, cells or tissues, and allow for the detection in vitro, ex vivo or in vivo using PET scanning (Positron Emission Tomography) of tumors, cells or tissues that express TRPV6 (Cheng et al. J. Nucl. Med. 48:987-994, 2007). Similarly, microvesicles sloughed of from TRPV6-rich tumors and present in the blood, other bodily fluids and excreta, can be detected by $^{18}$F-derivatives of the TRPV6-binding peptides.

In an additional embodiment, TRPV6-binding peptides conjugated with $^{125}$I-containing biomolecules target such compounds to TRPV6-expressing tumors, cells or tissues in vitro, ex vivo or in vivo to allow for detection using radiometric methods of these tumors, cells or tissues (Bolton et al. Biochem. J., 133, 529-539, 1973). Similarly, microvesicles sloughed off from TRPV6-rich tumors and present in the blood, other body fluids or excreta can be detected by using the compounds described herein.

In some embodiments, the compounds disclosed herein include a biomolecule that is a therapeutic agent. As used herein, a "therapeutic agent" is a substance used in the treatment, cure, prevention or suppression of a disease, disorder or medical condition. A therapeutic agent may also be used in the treatment, cure prevention or suppression of any symptoms associated with a disease, disorder or medical condition.

In some embodiments, the therapeutic agent is an anti-cancer agent. Examples of anti-cancer agents include, but are not limited to, taxane-based drugs, platin-based drugs, anthracyclines (e.g. doxorubicin, cyclophosphamide), topoisomerase II inhibitors (e.g. etoposide), alkylating agents (e.g. ifosfamide) plant alkaloids (e.g. vinorelbine), and antimetabolites (e.g. fluorouracil).

In some embodiments, the biomolecule is a small drug molecule, oligosaccharide, antibody, antibody epitope, nanometallic cluster, radioactively-labeled molecule, taxane-based drug, anthracycline-type drug, platin-based drug, antibiotic, anti-cancer drug, anti-fungal, anti-viral or anti-retroviral, or boron complex.

In some embodiments, the compound comprises a TRPV6-binding peptide attached to a biomolecule through a spacer. In one embodiment, the biomolecule is a protein or peptide and the compound is a fusion protein of the TRPV6-binding peptide and the biomolecule. Optionally, the fusion protein includes a peptide spacer between and the TRPV6-binding peptide and the biomolecule.

The invention also includes an isolated nucleic acid encoding a TRPV6-binding peptide of the invention, such as a nucleic acid encoding SEQ ID NO:1 or one of its fragments described herein. The invention also relates to isolated antibodies against a peptide of the invention. In one embodiment, the antibody optionally selectively binds a peptide of the invention, but does not bind to soricidin.

Compounds of TRPV6 Antibodies Conjugated to a Biomolecule

In another aspect, there are provided compounds comprising a TRPV6 antibody conjugated to a biomolecule. These compounds may be generated and used as described herein for compounds comprising TRPV6-binding peptides conjugated to a biomolecule. For Example, TRPV6 antibodies may be conjugated to a biomolecule, such as a detectable label or anti-cancer agent, either directly or through a spacer.

As shown in Examples 3 and 25, antibodies to TRPV6 and the fluorescently labeled TRPV6-binding peptide SorC27-cy5.5 co-localize in HEK293 cells expressing recombinant TRPV6 as well as in samples of Grade II serous papillary adenocarcinoma.

Detection of TRPV6

The compounds described herein bind to TRPV6 calcium channels and in some embodiments are useful to identify calcium channels in cells, tissues, tumors or microvesicles. In some embodiments, the peptides are useful to identify cells, tumors, tissues or microvesicles that do not express TRPV6. In a further embodiment, the peptides are useful to identify or label cells, tissues tumors or microvesicles that express large quantities of calcium channels. In one embodiment, the compounds described herein are useful for quantifying the amount of TRPV6 in a sample.

Accordingly, some embodiments described herein include a method for detecting TRPV6 protein in a sample comprising contacting the sample with a TRP-binding compound as described herein and detecting the TRPV6-binding compound. In one embodiment, the TRPV6-binding compound can be detected using an antibody that selectively binds to the TRPV6-binding peptide.

The compounds described herein that include a detectable label are also useful to detect TRPV6 protein or cells, tissues, tumors or microvesicles that express TRPV6 protein. Accordingly, embodiments described herein include methods for detecting TRPV6 protein in a sample comprising contacting the sample with any one of the compounds comprising a detectable biomolecule described herein and detecting the biomolecule conjugated to the TRPV6-binding peptide.

As used herein "sample" refers to biological sample representative of an organism or part of an organism. Examples of samples include, but are not limited to, biological fluids, blood, tissue samples, tissue biopsies, samples taken from tissue culture, biological fluids, tissue extracts, freshly harvested cells, microvesicles and lysates of cells which have been incubated in cell cultures. A "sample" may also refer to a defined area or volume of an organism, in vivo or ex vivo, such as an sample volume or area for magnetic resonance imaging. In one embodiment, the sample is an in vitro sample from a subject, such as a blood sample taken from the subject.

As used herein, the phrase "contacting the sample" typically includes, but is not limited to, mixing or incubating a compound as described herein with the sample, and the sample may include additional components such as a buffer, solution or test reagent. "Contacting the sample" may also include injecting or administering a compound described herein to an organism.

Identification and Diagnosis of Cancer

TRPV6 has been shown to be overexpressed in a number of cancer cell lines. The TRPV6-binding compounds disclosed herein are therefore useful for detecting cells that have over-expressed TRPV6 and accordingly the identification or diagnosis of tumors or cancer in vivo, ex vivo or in vitro.

Figure 6:
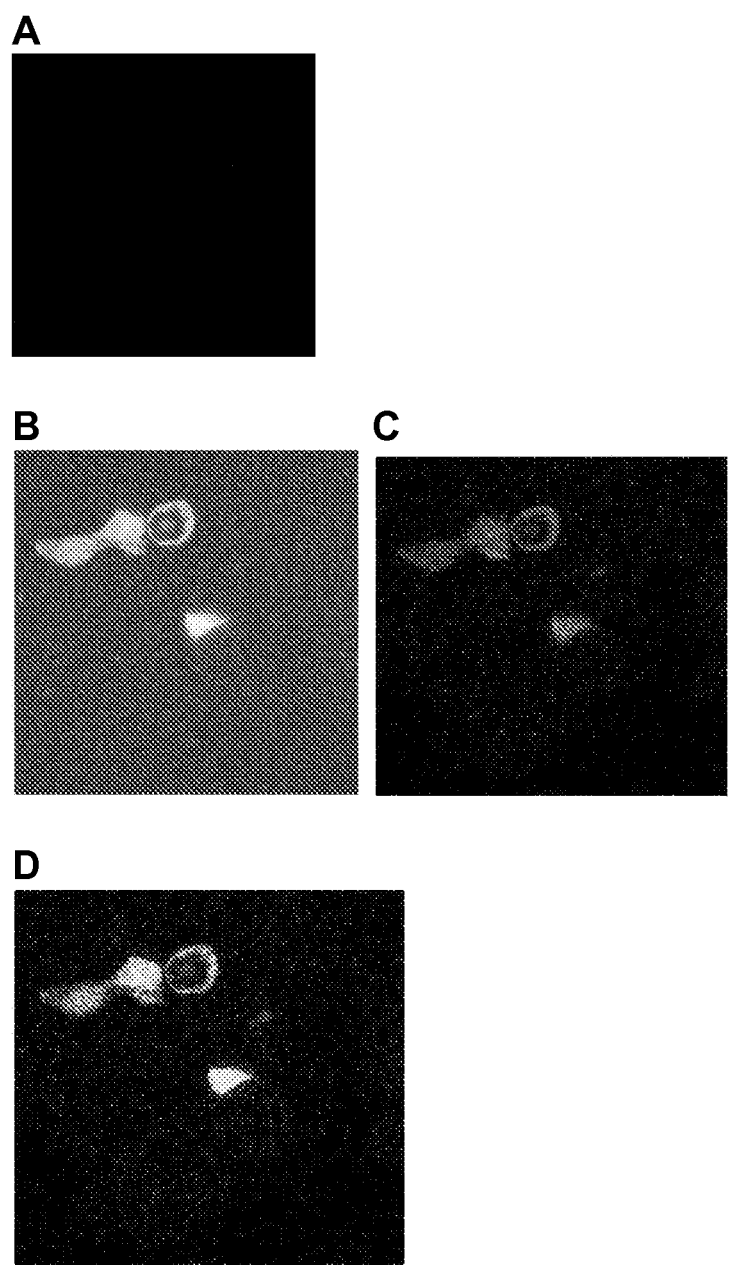
FIG. 6 shows the co-localization of TRPV6 protein expressed in HEK-293 cells with antibody to TRPV6 and with SorC27-cy5.5. HEK293 cells not transfected with the TRPV6 expression vector show no fluorescence when incubated with SorC27-cy5.5 (FIG. 6A, negative control).
Figure 7:
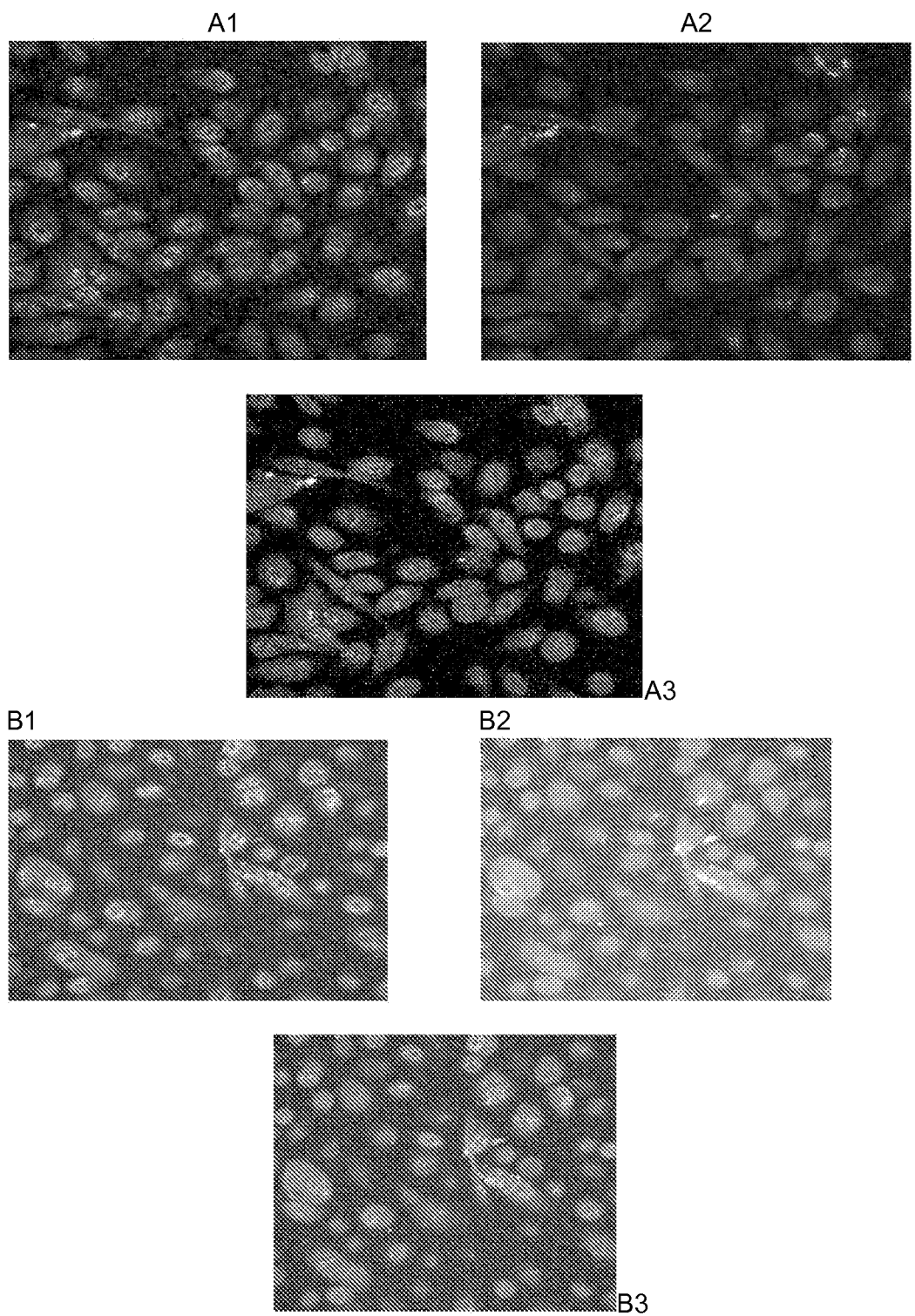
FIG. 7 shows the co-localization of SorC27-cy5.5 and fluorescently labeled TRPV6 antibodies in prostate cancer cell line PC-3. The A series of images shows A1: TRPV6-antibody immunofluorescence, A2: labeling with SorC27-cy5.5 and A3: overlap of A1 and A2. The B series of images shows PC-3 cells in the same sequence as the A series, but now transfected with a TRPV6 expression vector to increase the level of TRPV6 expressed by the cells. Both series of images show co-localization of SorC27-cy5.5 and TRPV6. The level of TRPV6 immunofluorescence and SorC27-cy5.5 fluorescence are both increased in the transfected cells with increased TRPV6 expression shown in the 7B series of Figures compared to the cells in the 7A series of Figures.
Figure 8:
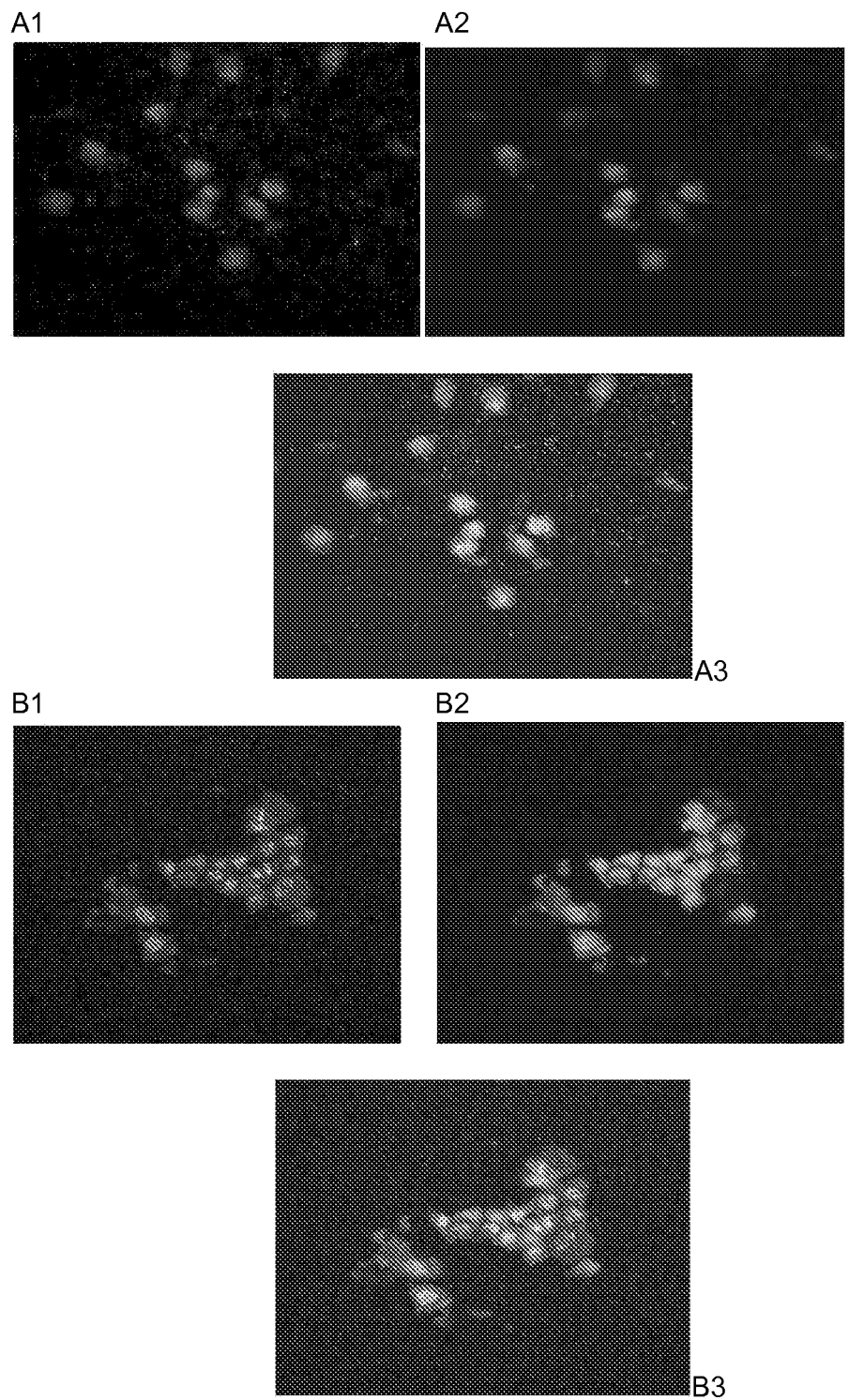
FIG. 8 shows the co-localization of SorC27-cy5.5 and fluorescently labeled TRPV6 antibodies in breast cancer cell line T 47D. The A series of images shows A1: immunofluorescence, A2: labeling with SorC27-cy5.5 and A3: overlap of A1 and A2. The B series of images shows PC-3 cells in the same sequence as the A series, but now transfected with a TRPV6 expression vector to increase the level of TRPV6 expressed by the cells. Both series of images show co-localization of SorC27-cy5.5 and TRPV6. The level of TRPV6 immunofluorescence and SorC27-cy5.5 fluorescence are both increased in the transfected cells with greater TRPV6 expression shown in the 8B series of Figures compared to the cells in the 8A series of Figures.
Figure 9:
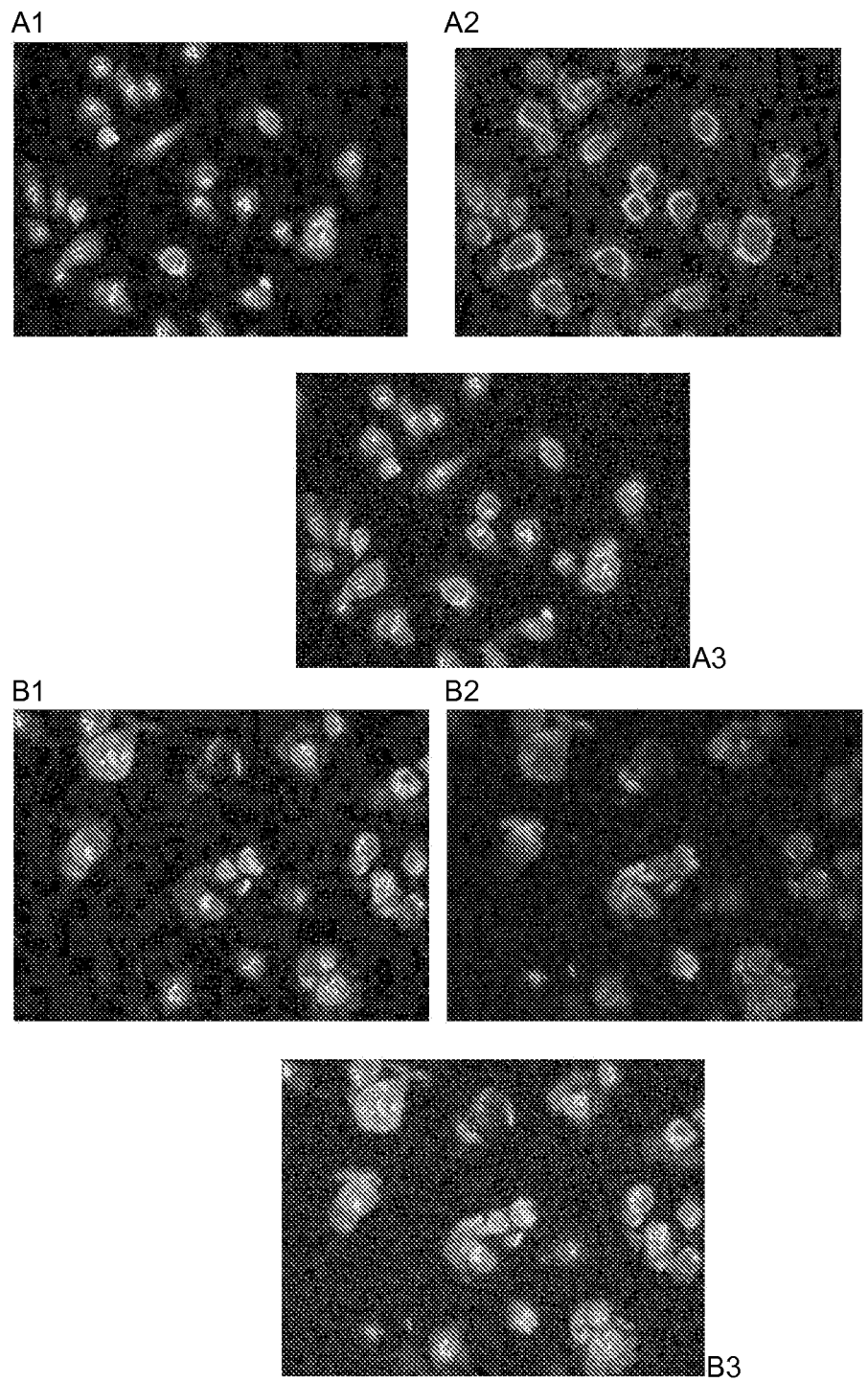
FIG. 9 shows the co-localization of SorC27-cy5.5 and fluorescently labeled TRPV6 antibodies in ovarian cancer cell line SKOV-3. The A series of images shows A1: immunofluorescence, A2: labeling with SorC27-cy5.5 and A3: overlap of A1 and A2. The B series of images shows PC-3 cells in the same sequence as the A series, but now transfected with a TRPV6 expression vector to increase the level of TRPV6 expressed by the cells. Both series of images show co-localization of SorC27-cy5.5 and TRPV6. The level of TRPV6 immunofluorescence and SorC27-cy5.5 fluorescence are both increased the transfected cells with greater TRPV6 expression shown in the 9B series of Figures compared to the cells in 9A series of Figures.

The TRPV6-binding compounds described herein have been shown to bind to and co-localize with TRPV6 in vitro. As shown in FIG. 6 and Example 3, a compound comprising SorC27 conjugated to an infrared fluorescent tag binds to TRPV6 expressed in HEK293 cells by transfection of the cells with an expression vector, but not to HEK293 cells without a transfected vector expressing TRPV6. FIG. 6 also shows that the TRPV6-binding compound co-localizes with a fluorescently labeled antibody to TRPV6. FIGS. 7-9 further show that SorC27 co-localizes with TRPV6 in prostate cancer cell line PC-3, breast cancer cell line T 47D and ovarian cancer cell line SKOV-3.

Figure 10:
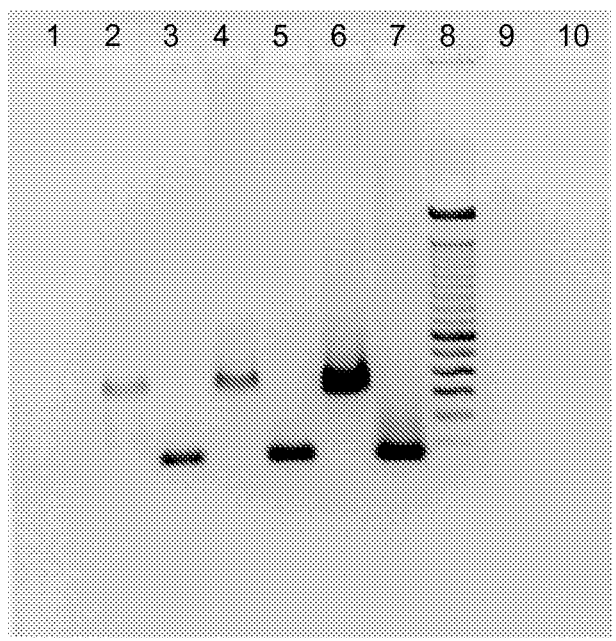
FIG. 10 shows the PCR detection of TRPV6 cDNA present in cDNA libraries made from total RNA extracted from a number of human ovarian tumor biopsies. Lane 1: Blank; 2: LTL320 TRPV6; 3: LTL320 β-actin; 4: LTL317 TRPV6; 5: LTL317 β-actin, 6: LTL269 TRPV6; 7: LTL269 β-actin, 8: 100 base pair ladder; 9: TRPV6 negative control; 10: β-actin negative control, The ranking of the band densities of the 3 TRPV6 amplicons for as reported in Table 1 is: LTL320 (+); LTL317 (+++); LTL269 (++++). The TRPV6 amplicon is at approximately 370 base pairs and the β-actin amplicon is at 50 base pairs.

TRPV6 is expressed in samples taken from human ovarian tumor biopsies. As shown in FIG. 10 and Example 4, TRPV6 transcripts were identified in cDNA libraries from human ovarian tissue tumor biopsies. The amount of TRPV6 in each sample was estimated and also quantitatively measured by densitometry with respect to the levels for the housekeeping gene β-actin. Table 1 provides the tumor type, ratio of TRPV6/β-actin and qualitative TRPV6 level for 18 patients with ovarian tumors.

TABLE 1

The relative amounts of TRPV6 transcripts in 18 human ovarian tumor biopsies detected by PCR of cDNA libraries produced from the tumors, and a ratio of the integrated band density of the TRPV6 amplicon to that of the house keeping gene β-actin.

| Patient Code | Ovarian tumour type | Ratio of density TRPV6/b-actin | Qualitative TRPV6 level |
|---|---|---|---|
| LTL-175 | clear cell carcinoma | 1.1 | ++++ |
| LTL-205 | serous adenocarcinoma | 0.2 | ++ |
| LTL-234 | mucinous carcinoma | 0.8 | +++ |
| LTL-237 | serous adenocarcinoma | 0.4 | ++ |
| LTL-246 | serous carcinoma | 1.8 | ++++ |
| LTL-247 | serous adenocarcinoma | 0.3 | +++ |
| LTL-258 | serous adenocarcinoma | 0.5 | +++ |
| LTL-259 | serous adenocarcinoma | 0.4 | ++ |
| LTL-260 | Carcinoma undifferentiated | 0.5 | +++ |
| LTL-269 | serous adenocarcinoma | 1.8 | +++++ |
| LTL-273 | endometrioid adenocarcinoma | 0.6 | +++ |
| LTL-284 | serous borderline | 0.5 | ++ |
| LTL-290 | serous carcinoma | 2.9 | +++ |

TABLE 1-continued

The relative amounts of TRPV6 transcripts in 18 human ovarian tumor biopsies detected by PCR of cDNA libraries produced from the tumors, and a ratio of the integrated band density of the TRPV6 amplicon to that of the house keeping gene β-actin.

| Patient Code | Ovarian tumour type | Ratio of density TRPV6/b-actin | Qualitative TRPV6 level |
|---|---|---|---|
| LTL-300 | endometrioid adenocarcinoma | 1.1 | +++ |
| LTL-305 | clear cell carcinoma | 0.3 | + |
| LTL-315 | serous carcinoma | 0.5 | ++ |
| LTL-317 | clear cell carcinoma | 0.4 | ++ |
| LTL-320 | not known at this time | 0.4 | + |

Figure 11:
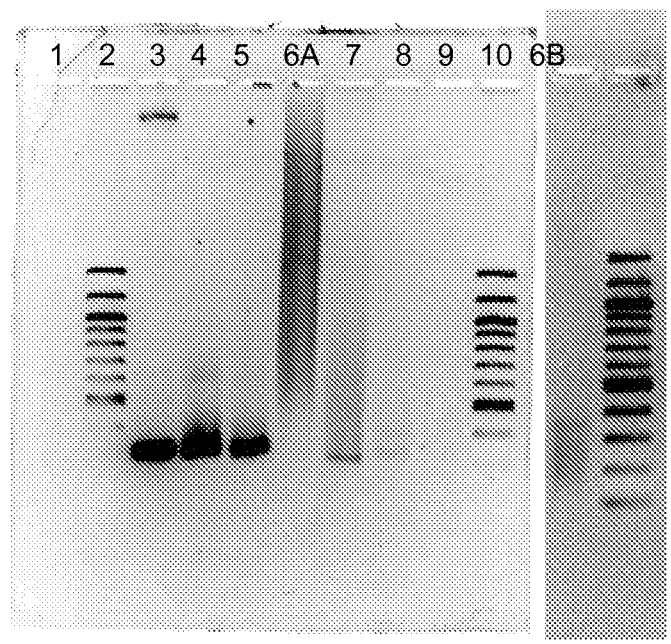
FIG. 11 shows the PCR detection of TRPV6 cDNA present in cDNA libraries made from total RNA extracted from a number of human ovarian cancer cell lines. Lane 1—Blank; 2-100 base pair ladder; 3-Positive control; 4—OVCAR3; 5—SKOV3 6A—OVC13 badly degraded, 6B OVC13 repeat showing some TRPV6 signal; 7—HEYC2; 8—OV2008; 9-Negative control; 10-100 bp ladder. The TRPV6 amplicon is at approximately 370 base pairs. Lanes 7 and 8 were isolated from very small sample sizes (low cell count) and thus show weak signals.

TRPV6 cDNA was also identified in a number of cDNA libraries prepared from total RNA extracts of human ovarian cancer cell lines including OVCAR3, SKOV3, OVC13, HEYC2, and OV2008 as shown in FIG. 11.

Figure 12A:
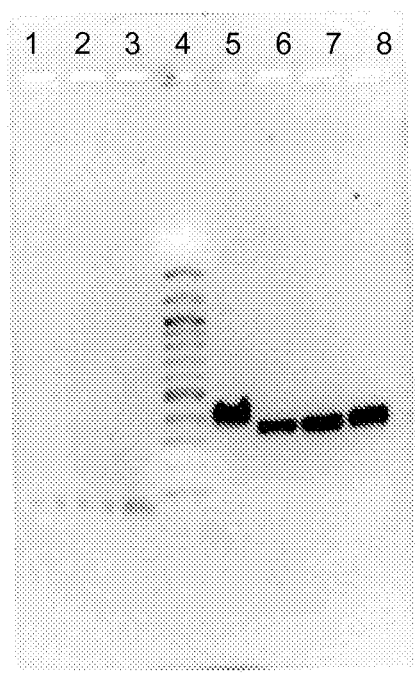
FIG. 12A shows the PCR detection of TRPV6 cDNA present in cDNA libraries made from total RNA extracted from a number of human breast cancer cell lines. Lane 1: HCC1954 β-actin; 2: T47D β-actin; 3: MCF10A β-actin; 4: 100 base pair ladder; 5: HCC1954 TRPV6; 6: T 47D TRPV6; 7: contaminated sample; 8: TRPV6 positive control from a TRPV6-containing expression vector (pcAGGS-TRPV6).
Figure 12B:
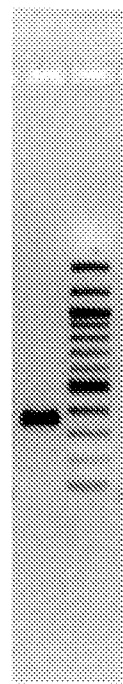
FIG. 12B shows the PCR detection of TRPV6 cDNA present in cDNA libraries made from total RNA extracted from the human breast cancer cell line MB423 (to the right of the 100 bp ladder). The TRPV6 amplicon is at approximately 370 base pairs.

TRPV6 expression was also determined in relation to the expression of the housekeeping gene β-actin in a series of breast cancer lines including T47D, HCC1954 and MB468 as shown in FIGS. 12A and 12B. The TRPV6 mRNA status results with respect to a number of breast cancer cell lines and ovarian cancer cell lines is shown in Table 2:

TABLE 2

TRPV6 mRNA status of human breast and ovarian cancer cell lines.

| | TRPV6 mRNA status |
|---|---|
| Breast Cancer Cell Lines | |
| MB 231 | Positive |
| MB468 | Positive |
| T 47D | Positive |
| HCC1954 | Positive |
| MCF 7 | Positive |
| Ovarian Cancer Cell Lines | |
| OVCar-3 | Positive |
| SKOV-3 | Positive |
| OV 90 | Positive |
| HeyC2 | Positive |
| OV 2008 | Positive |
| OV C13 | Positive |

Figure 13:
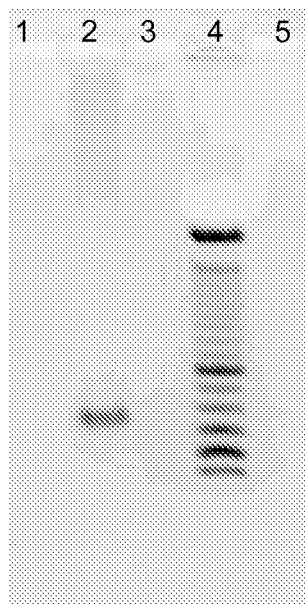
FIG. 13 shows PCR detection of TRPV6 cDNA present in cDNA libraries made from total RNA extracted from a human prostate cancer cell line (PC-3). The TRPV6 amplicon is at approximately 370 base pairs. The molecular weight ladder is a 100 bp ladder. Lane 1: Blank; Lane 2.

TRPV6 cDNA was also detected in a cDNA library made from a human prostate cancer cell line as shown in FIG. 13.

In addition, TRPV6 protein levels were shown to be over-expressed in a number of different cancer cell lines and ovarian tumor samples as shown in FIGS. 14-16 and Example 5.

Accordingly, embodiments disclosed herein include a method for identifying or diagnosing cancer in a test sample from a subject comprising detecting TRPV6 mRNA or protein in the test sample and optionally comparing the amount of TRPV6 mRNA or protein in the test sample with a control sample. In one embodiment, an increased amount of TRPV6 mRNA or protein in the test sample compared to the control sample is indicative of cancer. In one embodiment, a minimal increase of at least 10% is indicative of cancer. In another embodiment, an increased amount of at least: 20%, 50%, or 100% of mRNA or protein in the test sample compared to the control sample is indicative of cancer. In some embodiments, an increase of 3-times the amount of TRPV6 mRNA or protein in the test sample compared to the control sample is indicative of cancer. Examples of tissues where TRPV6 would be present in the control are colon, kidney, prostate and breast. In other tissues, such as any endothelial-derived tissues, TRPV6 is not expressed at all, so detection of the presence of TRPV6 mRNA or protein in the test sample is indicative of the presence of cancer. Optionally, such methods are performed on such tissues by detecting TRPV6 in the test sample, without also using a control sample comparison.

TRPV6 rich tumours are nearly exclusively of epithelial origin although some prostate cancer cell lines such as DU145 do not express TRPV6. Types of cancer that are TRPV6-rich include, but are not limited to, ovarian, breast, prostate, liver, endometrial, glial, colon, pancreatic, and leukemia cancers.

In some embodiments, the subject is a mammal, such as a human. In some embodiments, the methods described herein are used in vivo, ex vivo or in vitro.

As used herein, the term "control sample" includes any sample that can be used to establish a base or normal level, and may include samples taken from healthy persons or tissues. In some embodiments, the "control sample" is a predetermined standardized control. In some embodiments, the "control sample" is a pre-determined value, threshold or range.

As used herein, the phrase "identifying cancer" includes the detection of cells in a sample from a subject that have lost normal control mechanisms and have unregulated proliferative growth. Optionally, "identifying cancer" in a sample from a subject can refer to diagnosing cancer in the subject.

In one embodiment, the methods described herein can be used to provide further information regarding a tumor or cancer. Determination of cancer stage or type typically includes the determination of information regarding the stage of cancer (e.g. tumor stage) or type of cancer. In one embodiment, cancer stage is determined as known in the art using the Tumor, Node, Metastasis (TNM) system. T (for Tumor) reflects on the size of the primary tumor and where it is located; N (for node) reflects on whether the tumor has spread to lymph node; and, M (for Metastasis) reflects on whether the cancer has metastasized (See for example *AJCC Cancer Staging Manual*, Seventh Edition (2010) published by Springer-Verlag New York, herein incorporated by reference). For example, in one embodiment the cancer is ovarian cancer and the following staging guidelines may be used:

Stage I (in ovaries): T1, N0, M0 with sub-stages I A, B, C (where N and M remain "0")

Stage II (in one or both ovaries, pelvic invasion): T2, N0, M0 with sub-stages II A, B, C (where N and M remain "0")

Stage III (in ovaries, pelvic region and spread into peritoneal area >2 cm: T3 N0, M0 with sub-stages III A, B, C (where N and M remain "0"); Stage IIIC (into lymph): T, N1, M0

Stage IV (spread to distant organs): any T, any N, M1

Optionally, the methods described herein are useful to further characterize a tumor by providing an estimation of tumor volume, tumor location, or tumor type. In some embodiments, the diagnosis of cancer includes obtaining therapy response information such as to determine the result of a course of anti-cancer therapy on tumor size typically measured as tumor volume.

As shown in Example 24, levels of TRPV6 are higher in tissue samples from subjects with cancer compared to samples of normal tissue. More specifically, FIG. 18 and Table 3 show that tissue micro-array samples of Grade I, II and III serous papillary adenocarcinoma exhibited more expression of TRPV6 compared to samples of normal ovarian tissue. TRPV6 levels are useful to distinguish between early stage Grade I cancers compared to normal samples. Accordingly, detection of TRPV6 using antibodies or using the TRPV6-binding peptides described herein is useful to identify or diagnose subjects with cancer or with a greater likelihood of developing cancer. Optionally, levels of TRPV6 expression are useful to grade cancers or identify more aggressive forms of cancer.

In some embodiments, methods described herein are used to identify or diagnose breast cancer, ovarian cancer, blood cancer, brain cancer, retinal cancer, liver cancer, thyroid cancer, colon cancer, prostate cancer, pancreatic cancer, glial cancer or endometrial cancer.

In one embodiment, measuring the expression of the trpv6 gene, through measurement of the amount of TRPV6 mRNA or corresponding cDNA transcripts produced in a sample or cell line cell provides a diagnostic tool with which to identify cancer in a sample. In some embodiments, the presence or amount of TRPV6 mRNA or transcripts in a sample from a subject is used to diagnose or indicate the stage of cancer in the subject. For example, FIG. 24 shows that the relative levels of TRPV6 mRNA in blood is significantly higher in subjects with cancer compared to levels in healthy controls. Accordingly, in one embodiment the presence or amount of TRPV6 mRNA or transcripts in a sample from a subject is useful to identify cancer in a subject. In one embodiment, the presence or amount of TRPV6 mRNA or transcripts in a sample is useful to identify ovarian, breast or prostate cancer in a subject.

As shown in FIG. 25, the relative amount of TRPV6 protein is also higher in samples of plasma from subjects with stage I or II ovarian cancer compared to healthy controls. Accordingly, in one embodiment the detection of the TRPV6 protein is useful to identify cancer in a subject. For example, in one embodiment levels of TRPV6 protein in a test sample from a subject are compared to levels of TRPV6 protein in a corresponding sample from a healthy control, wherein higher levels of TRPV6 in the test sample are indicative of cancer. In one embodiment, the test sample is a blood or plasma sample and a TRPV6 level that is twice as high as the level in a corresponding sample from a healthy control is indicative of cancer.

Figure 1:
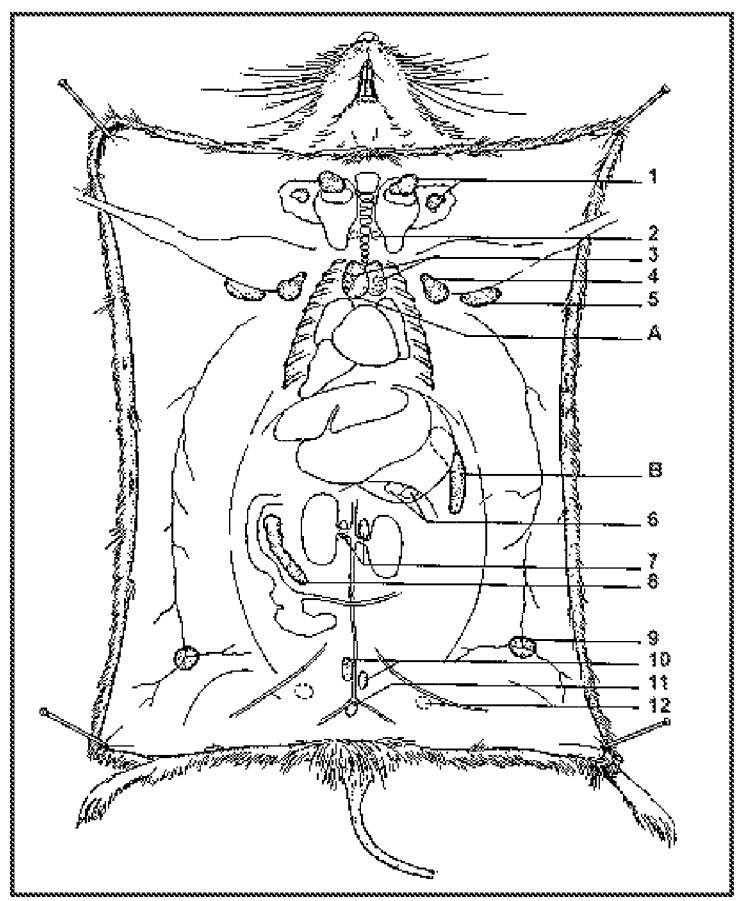
FIG. 1 is a line drawing showing the location of the lymph nodes in the mouse. Significant accumulation of SorC13-Cy5.5 compound and SorC27-Cy5.5 compound four hours after i.v. injection of 100 ug of each of the labeled peptides into CD1 mice was observed in the following nodes labeled in FIG. 1: 1. Superfacial cervical nodes; 4. Axillary nodes; 5. Branchial nodes; 8. Mesenteric nodes; 9. Inguinal nodes.
Figure 2:
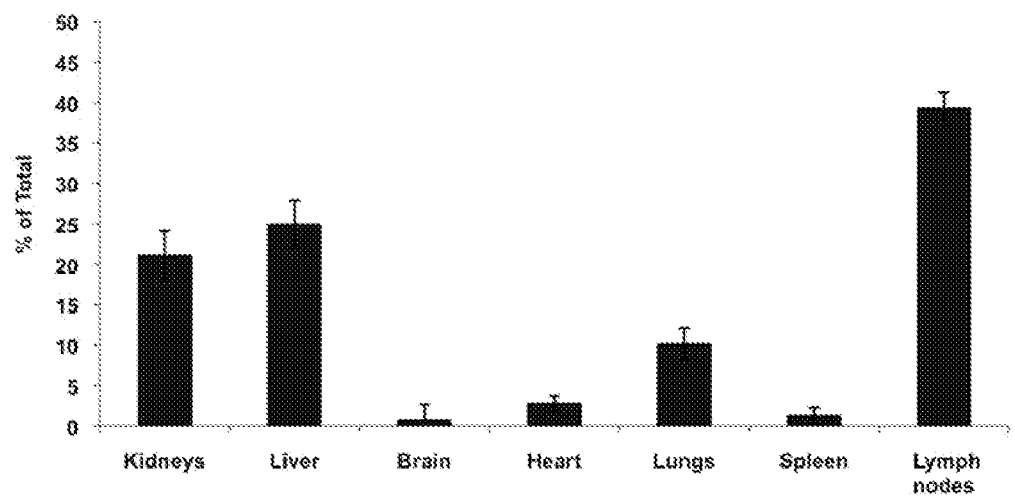
FIG. 2 shows the distribution of SorC13-Cy5.5 compound in CD1 mice 4 hours after i.v. injection. The Y-axis is the percentage of total fluorescence measured in all tissues.
Figure 3:
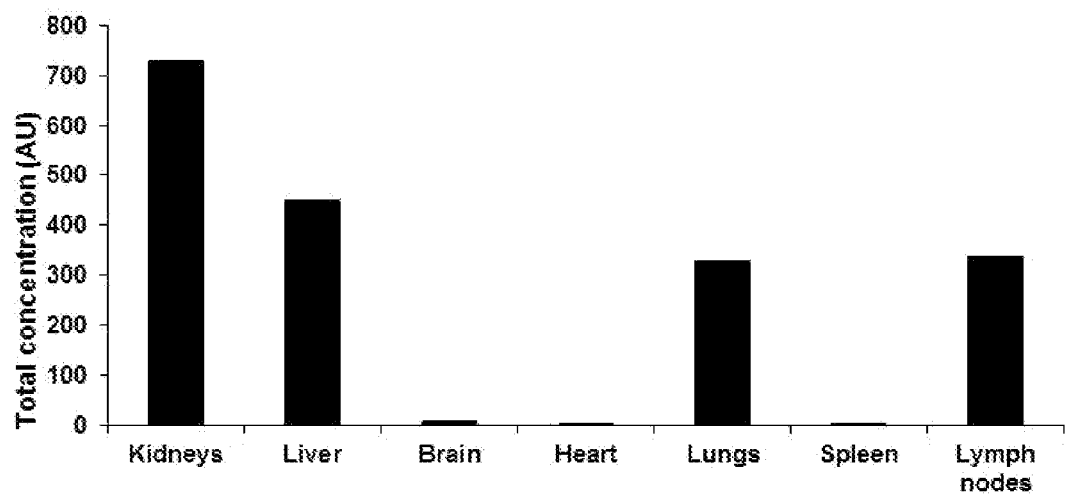
FIG. 3 shows the distribution of SorC27-Cy5.5 compound in CD1 mice 4 hours after i.v. injection. The Y-axis is the total fluorescence measured in each tissue.

As set out in Example 1 and FIGS. 1 to 3, the TRPV6-binding peptides localize predominantly in lymph nodes, but also in lung, liver and kidney, which are common sites where metastatic cancer is located. Accordingly, the TRPV6-binding peptides described herein are useful for detecting and binding to metastatic cancer, including glioblastomas and cancers that have spread to the lung, liver, kidney, spleen, pancreas and bone marrow.

The peptides and compounds described herein are particularly useful for detecting and binding to lymph node metastases. "Lymph node metastases" optionally include lung cancer (Mujoomdar et al, 2007), gastric cancer, cervical carcinoma (Lyshchik et al., 2007), vulvar carcinoma (Vernooij et al, 2007), endometrial cancer (Aalders et al, 2007), head and neck squamous cell carcinoma (Veness et al., 2007), esophagus and throat cancer, nasopharyngeal carcinoma (Ma et al., 2007), gastrointestinal cancer (Wind et al., 2006), Gall bladder cancer, brain cancer (Mujoomdar et al., 2007), thyroid cancer, breast cancer, ovarian cancer, prostate cancer, glial cell cancer and colorectal cancer. The peptides of the invention are therefore useful in detecting cancer in a mammal at any of cancer stages I, II, III or IV.

The TRPV6-binding peptides and compositions described herein are also useful for detecting intact TRPV6 channels present in microvesicles sloughed off from tumors, circulating in the blood or cancer cells circulating in the blood. In some embodiments, microvesicles sloughed off from TRPV6-expressing tumors, or cancer cells circulating in bodily fluids or excreta, are detected by PCR-based (e.g. RT-PCR or Q-RT-PCR) or antibody-based methods (e.g. Western blotting, immunofluorescent detection in biopsies or bodies such as cells or microvesicles in bodily fluids or excreta). For example, intact microvesicles derived from tumor cells and present in a bodily fluid or excreta would show a population of TRPV6 channels when treated with TRPV6 antibodies or TRPV6-binding peptides conjugated with a detectable biomolecule. For example, FIGS. 24 to 26 show that blood and plasma samples taken from subjects with cancer, including stage I cancer, have significantly higher levels of TRPV6 mRNA or protein compared to healthy controls. Testing bodily fluids such as blood or plasma for TRPV6 mRNA or protein therefore provides a relatively simple test for the early stage detection of cancer, compared to, for example, detecting tumors and testing tumor biopsies for the presence of cancer cells.

Antibodies developed to the TRPV6-binding peptides are useful to detect the TRPV6-binding peptide/TRPV6 complex in tumors, tissues or cells in vitro or ex vivo by tagging the TRPV6-binding peptide antibodies with a detectable entity (fluorescent tag, radioactive tag, etc.). Similarly, microvesicles sloughed of from TRPV6-rich tumors and present in bodily fluids or excreta are readily detected by such antibodies or conjugates of the TRPV6-binding peptides.

Drug Delivery and Method of Manufacture

The TRPV6-binding peptides and compounds described herein are useful to deliver biomolecules to tumors, cells or tissues that express TRPV6. As shown in Examples 26 and 28, TRPV6-binding peptides are able to target TRPV6 expressing cells and deliver compounds to tumor sites in vivo.

Accordingly, one embodiment includes a method of manufacturing a pharmaceutical compound by conjugating a biomolecule to a TRPV6-binding peptide. Biomolecules are readily conjugated to the TRPV6-binding peptides or antibodies to TRPV6-binding peptides, by methods known in the art, such as those set out in Examples 1,11-13, 16, 19-23, 26 and 28.

Biomolecules can be conjugated to the TRPV6-binding peptide by linking either directly or indirectly the TRPV6-binding peptide to the biomolecule. In one embodiment, the TRPV6-binding peptide is conjugated to Cy5.5 at the single cysteine thiol through a maleamide-activated reaction. In other embodiments, the biomolecule is liked to either the C-terminus, or N-terminus of the peptide. In other embodiments, the biomolecule is linked through any another suitable molecular site such as a functional group side chain of the peptide.

The biomolecule may also be conjugated to a TRPV6-binding peptide via chemical modification such as by an ester linkage or an amide linkage. Various methods of conjugating peptides to a biomolecule are disclosed for example in Peng Li et al., Biopolymers 87: 225-230, 2007; U.S. Pat. No. 6,348,317; and U.S. Application Nos. 20070218502 and 20070020264.

In another aspect, there is provided a method of manufacturing a pharmaceutical compound comprising conjugating a biomolecule to a TRPV6 antibody.

Another embodiment includes a method of delivering a pharmaceutical composition to a cell expressing TRPV6 comprising contacting the cell with a compound comprising i) TRPV6-binding peptide conjugated to a biomolecule and ii) a carrier. The methods of delivering a pharmaceutical composition include methods for delivering the compositions comprising the TRPV6-binding peptides described herein.

In one embodiment, the compounds optionally comprise a TRPV6-binding peptide chemically altered to deliver nano-metallic clusters to tumors, tissues or cells (for example, gold nano-particles, nano-spheres, nano-tubes or other nano-constructs) that, when irradiated with electromagnetic radiation, heat and kill cells in the vicinity of the metallic cluster.

In another embodiment, the compound comprises TRPV6-binding peptides that are chemically altered to deliver boron clusters (e.g. closo-boron, a cluster containing 12 boron atoms) which, when irradiated with slow thermal neutrons, produce energetic alpha particles that kill nearby cells.

Other compounds comprise TRPV6-binding peptides of the invention chemically altered to deliver to TRPV6 producing tumors, cells or tissues, antigens that serve to recruit pre-existing antibodies to the TRPV6-rich tumors, tissues or cells. This, in turn, would mark cancers for destruction by the immune cell system.

The compounds described herein are also useful to deliver to TRPV6 producing tumors, cells or tissues, novel antigens toward which monoclonal antibodies are specifically developed and administered with the result being antibody tagging of TRPV6-rich cancers. This would mark cancers for destruction by the immune cell system.

The compounds described herein are also useful to deliver covalently attached radioactively labeled molecules to that deliver a therapeutic radiation dose to tumors, tissues or cells rich in TRPV6 channels.

The compounds described optionally deliver to TRPV6-producing tumors, cells or tissues, covalently attached therapeutics such as the taxane-based drugs, anthracyline-type drugs, platin based drugs or any other therapeutic molecule. The methods and compounds described herein are also useful to deliver anti-biotics, anti-fungals, anti-virals and anti-retrovirals or any other therapeutic drug to cells that express TRPV6 or to lymph nodes, lung, liver and/or kidney.

Detection of Cancer Tumors in a Subject

As shown in Examples 26 and 28 and corresponding FIGS. 21 and 23, detection of TRPV may be used to identify a cancer tumor in a subject in vivo. As used herein "identifying a cancer tumor" refers to localizing or detecting a region in a sample or subject that has a cancer tumor. As used herein, "cancer tumor" refers to a neoplasm or a solid lesion formed by the abnormal growth of cells that have lost normal control mechanism and have unregulated proliferative growth. A number of cancers have been shown to overexpress TRPV6 and therefore generate TRPV6-rich tumors (see Examples 4 and 5). Accordingly, in one aspect there is provided a method for detecting a cancer tumor comprising administering to a subject a compound comprising a TRPV6-binding peptide or an antibody to TRPV6. Preferably, the compounds also include a detectable label that facilitates the detection of TRPV6 in the subject. For example, in one embodiment the TRPV6-binding peptide is SorC27, and the detectable label is Cy5.5. In another embodiment, the TRPV6-binding peptide is conjugated to a magnetic resonance imaging (MRI) contrast agent such as super-paramagnetic iron oxide and MRI is used to detect regions in a sample or subject with increased levels of TRPV6. Regions of the subject that exhibit increased levels of TRPV6 are indicative of a TRPV6-rich tumor in that region. Mathematical models that compare the distribution of TRPV6 across the subject are readily applied to identify specific regions of the subject that have increased levels of TRPV6 that are indicative of a TRPV6-rich tumor. In some embodiments, an average level of TRPV6 observed throughout a subject is used to normalize the TRPV6 levels and identify specific regions with increased expression of TRPV6. In other embodiments, levels of TRPV6 are compared to a pre-standardized control level or to levels observed in corresponding regions in subjects known not to contain TRPV6-rich cancer tumors.

A person skilled in the art will appreciate a number of imaging techniques and corresponding detectable labels are suitable for detecting TRPV6-rich tumors in accordance with the present description. For example, the TRPV6-binding peptides are optionally radioactively labeled and detected using a scintillation counter. Alternatively, the TRPV6-binding peptides are fluorescently labeled and detected using an optical detection system. In one embodiment, the TRPV6-binding peptides are conjugated with a contrast agent. As used herein, a "contrast agent" is a substance used to enhance the contrast of structures or cells within a sample of subject in medical imaging. In one embodiment the contrast agent is a MRI contrast agent, such as an agent that alters the T1 or T2 relaxation time of protons located nearby. Examples of MRI contrast agents include paramagnetic gadolinium, paramagnetic manganese, or super-paramagnetic iron oxide (SPIO).

Additional Properties of the Peptides

The TRPV6-binding peptides of the compounds described herein, such as SorC13 and SorC27, are typically stable in aqueous solution at 4° C. for at least 3 weeks with no change in purity as measured by HPLC. As dry solids, the peptides are typically stable at −80° C. for at least 1.5 years.

The TRPV6-binding peptides also avoid a major adverse effects of pharmaceuticals related to the ability of a substance to cross the central nervous system protective barrier, the blood-brain barrier. The inability of the peptides of the invention to cross this protective barrier obviates the potential toxicity to the central nervous system.

The peptides of the invention, particularly the shorter peptides, such as SorC13, are typically less antigenic. Peptides having a number of amino acids equal to or less than the empirical cutoff for antigenicity (typically considered to be 13 amino acids for peptides in general) possess no antigenicity.

Some embodiments include pre-packaged kits that comprise some or all of the reagents necessary to perform any of the methods described herein. Optionally, the kits may include one or more control samples. In some embodiments the control sample is known to express or contain TRPV6 (a positive control). In other embodiments, the control sample is a negative control that is known not to express or contain TRPV6. In a further embodiment, the control sample is known to express or contain a certain level of TRPV6 or correspond to specific type or stage of cancer. In some embodiments the kits include at least one compound comprising a TRPV6-binding peptide as described herein, and a buffer solution. In some embodiments, the kits may include nucleic acid primers for amplifying or detecting TRPV6 mRNA in a polymerase chain reaction. In some embodiments, the kits can also include nucleotides, enzymes and buffers useful in the method of the invention as well as electrophoretic markers such as a bp ladder. In some embodiments, the kits will include detailed instructions for carrying out the methods described herein.

EXAMPLES

The following examples illustrate embodiments of the invention and do not limit the scope of the invention.

Example 1: Tissue Distribution of SorC13 and SorC27

SorC13 and SorC27 were labeled with the near-infrared probe, Cy5.5. SorC13 was labeled at lysine-1 and lysine-8 with the infrared fluorescent probe cy5.5 through reaction with Cy5.5 NHS ester-activated process. SorC27 was labeled at the single cysteine thiol with Cy5.5 maleimide-activated reaction. The labeled peptides were purified with a combination of size exclusion chromatography and HPLC. The label, Cy5.5, fluoresces in the infra-red region after excitation with a scanning laser. The low energy laser is able to penetrate the animal to about 1 cm and, thus, by scanning prone and supine positions, the presence of the tagged peptides can be quantified in three dimensions.

Cy5.5-labeled peptides were intravenously injected into CD1 mice (4 for each compound) at 100 ug per animal in 100 uL, and animals were imaged live using an optical imaging system, Optix eXplorer (GE Healthcare Systems) at different time points (30 min, 90 min, 4 h). Some animals were observed at 24 hours after perfusion to remove blood (and lymph). The bio-distribution of the labeled peptides in different organs and tissues were visualized and relatively quantified by optical imaging analysis. This protocol allows for visualization of the location of the labeled peptides and how the location changes over time. FIG. 1 shows the location of lymph nodes in the mouse. Nodes that accumulated the labeled peptides are indicated by line 1 (superfacial cervical nodes), line 4 (axillary nodes), line 5 (brachial nodes), line 8 (mesenteric nodes) and line 9 (inguinal nodes). FIGS. 2, 3 and 4 show the amounts of labeled peptides in various organs ex vivo. Combined, these experiments show that:

Neither of the C-peptides moved across the blood-brain barrier.

Tagged SorC13 and SorC27 localize predominantly in lymph nodes, lung, liver and kidney.

Tagged SorC13 and SorC27 were still detectable in these tissues after perfusion at 24 hours.

Measurement of the fluorescence life-time in various organs showed that metabolism of labeled peptides appears to be in liver and kidney as Cy5.5 has a shorted life-time than peptide/Cy5.5 adducts.

TRPV6-binding peptides are capable of targeting TRPV6 with a 'cargo' linked to the peptides that can be delivered to these tissues

Figure 5:
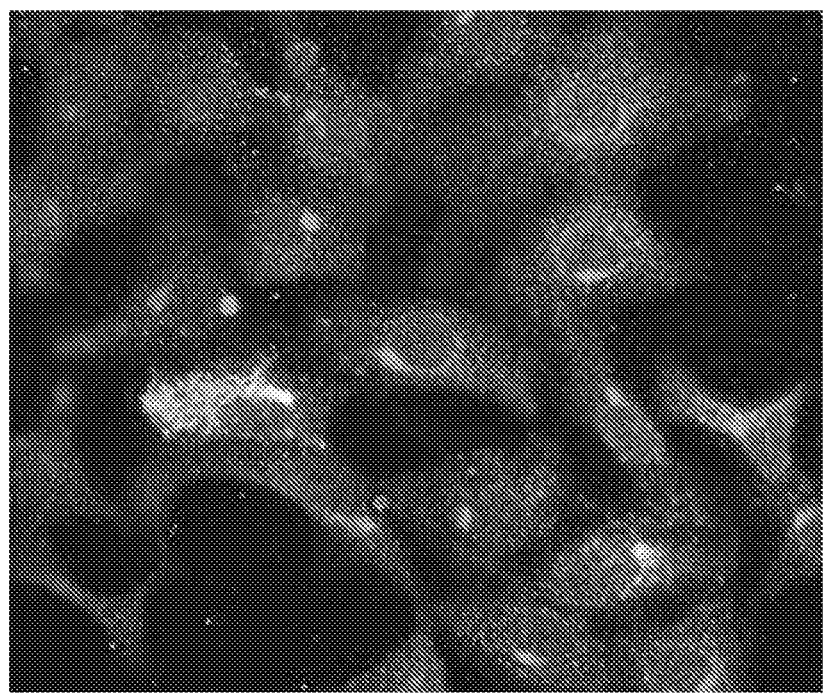
FIG. 5 shows the immuno-localization of TRPV6 in ovarian cancer cells (SKOV-3). SKOV-3 cells were transfected with a TRPV6-GFP fusion protein. Both endogenous TRPV6 and TRPV6-GFP were detected with a combination of a primary antibody to TRPV6 N-terminal region and a secondary antibody to IgG labeled with FITC (a green fluorescent label). One cell in the field shows co-localization of brightly fluorescent, transfected TRPV6-GFP protein and the antibody to TRPV6. The other cells (not transfected) in the field show the red fluorescence of wheat germ agglutinin marking the cell membrane, and the green fluorescence of immuno-localization indicating the secondary antibody labeled with FITC used to detect the primary anti-TRPV6 antibody.

Example 2: Co-Localization of TRPV6 Antibodies and Fluorescently-Labeled TRPV6 Expressed in Human Cancer Cells As shown in FIG. 5, TRPV6 expressed in a cancer cell line (SKOV-3) or in ex vivo samples is optionally detected using a primary antibody to the TRPV6 protein, followed by a secondary antibody that is, itself, detectable. Additionally cancers are readily detected by using the TRPV6-binding peptides conjugated or tagged with a detectable molecule. Alternatively, an antibody developed to the TRPV6-binding peptides is readily tagged with a detectable entity such as a fluorescent tag or radioactive tag.

As well, an antibody to the TRPV6-binding peptides is readily developed and used in traditional immunochemical fashion for tissues (in vitro), tumors, cells or microvesicles.

Example 3: Co-Localization of Fluorescently-Labeled TRPV6-Binding Peptides and Antibodies to TRPV6 in HEK269 Cells HEK-293 cells were transfected with a TRPV6 expression vector and incubated with fluorescently labeled antibodies to the N-terminal peptides of TRPV6 as well as fluorescently labeled SorC27 (SorC27-cy5.5). HEK-293 cells that were not transfected with a TRPV6 expression vector were also incubated with fluorescently labeled anti-TRPV6 and SorC27-cy5.5 as a negative control (FIG. 6A).

As shown in FIGS. 6B to 6D, SorC27-cy5.5 bound to TRPV6 as indicated by the co-localization of SorC27-cy5.5 and anti-TRPV6. This experiment shows that the compounds described herein target and bind to TRPV6 and further that compounds comprising a TRPV6-binding peptide conjugated to a biomolecule, are effectively localized to cells that express TRPV6.

Example 4: Expression of TRPV6 mRNA in Cancer Cell Lines and Tumor Biopsies as a Diagnostic for Cancer and for Staging Cancers As shown in FIGS. 10-13, polymerase chain reaction with primers directed towards TRPV6 transcripts detects up-regulation of TRPV6 mRNA in cDNA libraries produced from extracts of total RNA of cancer cells or biopsies of human cancerous tumors.

In order to quantify the relative amount of TRPV6 transcripts in a sample, transcripts were also amplified and detected for the housekeeping gene β-actin and the observed ratio of TRPV6 β-actin was recorded.

A common mechanism is in effect in all of the cancer types referenced herein, as they are all derived from epithelial tissues. Peng et al. showed in prostate cancer that normalized amounts of TRPV6 mRNA were about 2-fold greater in samples from subjects with Gleason scores of 5-7 as compared to samples with benign hyperplasia, and about 3-fold greater in samples with Gleason scores of 8-9.

FIGS. 10-13 show a significant increase in the expression of TRPV6 in samples of cancer lines such as ovarian cancer. The methods described herein that detect either TRPV6 mRNA or protein levels are therefore useful for the staging of cancers such as ovarian cancer.

Example 5: Analysis of TRPV6 Protein in Cancer Cells

Western blotting using antibodies developed to TRPV6 was used to detect the expression of TRPV6 protein in a number of cancer cells.

As shown in FIG. 14, TRPV6 protein was over-expressed in extracts from ovarian (SKOV-3), breast (T47D) and prostate cancer (PC-3) cell lines compared to extracts from a hepatoblastoma HEP G2 control cell line known to express TRPV6.

FIGS. 15A through 15D show that extracts from human ovarian tumors also overexpress TRPV6 protein and that TRPV6 is upregulated in ovarian tumors.

FIG. 16 shows that TRPV6 is over-expressed in extracts from human glioblastoma (U87MG), human colon (CaCo-2)

and pancreatic carcinoma cells (Panc1). Further, the degree of de-glycosylation in Panc1 increases with increase numbers of culture passaging.

Collectively the data in FIGS. 14 to 16 shows that TRPV6 protein is overexpressed in a number of cancer cells and ovarian tumor samples.

Example 6: Use of TRPV6 Antibodies to Determine Cancer Stages

Antibodies to TRPV6 are used to determine the stage of a tumor (e.g. ovarian tumors) using immunolocalization methods. Staged tissue microarrays of ovarian tumors are probed with fluorescently labeled-TRPV6 antibodies.
Results Experiments show that, as the stage of the tumor progresses through Stage I to Stage IV there is an increase in the density of the immunofluorescence signal indicating an increase in the population of TRPV6 channels in the tissues.

Example 7: Use of Fluorescently Tagged TRPV6-Binding Peptides to Determine Cancer Stages Fluorescently tagged TRPV6-binding peptides are useful to determine the stage of a tumor by direct incubation of Tissue Micro-Arrays (TMA) with the peptide reagent. SorC27-cy5.5 compound is incubated with cells from a subject and fluorescence levels are compared to levels from control staged tumor samples.
Results Experiments show that, as the stage of the tumor progresses through Stage I to Stage IV, there is an increase in the intensity of the fluorescent signal due to binding of the tagged compound comprising SorC27-tagged with cy5.5 to the increased population of TRPV6 channels.

Example 8: Use of Fluorescently Tagged Antibodies to Compounds Comprising TRPV6-Binding Peptides to Determine Cancer Stages Fluorescently tagged antibodies to TRPV6-binding peptides are used to detect TRPV6-binding peptides bound to TRPV6 channels of a validated ovarian cancer tissue microarray.
Results After incubating the TMA with one of the TRPV6-binding peptides, and then deploying a fluorescently tagged antibody developed against the TRPV6-binding peptides, there is a positive correlation between the intensity of the fluorescent signal with the stage of the cancer from Stage I through Stage IV.

Example 9: Fluorescently-Labeled TRPV6-Binding Peptides Bind to TRPV6-Rich Tumors Xenografted in Mice Mice xenografted with an ovarian TRPV6-rich tumor (SKOV-3 cells) are injected with the fluorescently-labeled TRPV6-binding peptide SorC27-cy5.5.
Results The ovarian tumors over-expressing the TRPV6 channel are detected in vivo by SorC27-cy5.5 compound after administration to mice in which TRPV6 tumors are xenografted (e.g. ovarian tumors). The TRPV6-rich xenografted tumor mass derived from SKOV-3 cells is clearly distinguished from the background tissue as strongly fluorescing in the far infrared.

Example 10: Use of Super Paramagnetic Iron Oxide-Labeled (SPIO) TRPV6-Binding Peptides to Detect TRPV6-Producing Cells A compound comprising TRPV6-binding peptide conjugated with Super Paramagnetic Iron Oxide such as SPIO-SorC27 is incubated with SKOV-3 cells (TRPV6 positive) and HEK293 cells (TRPV6 negative). The cells are then imaged using Magnetic Resonance Imaging.
Results SKOV-3 cells over-expressing the TRPV6 channel are detected in vitro by MRI enhancement agents such as SPIO-SorC27. The TRPV6-rich SKOV-3 cells are clearly distinguishable from the TRPV6-negative HEK293 cells by strongly enhanced magnetic resonance signals and imaging.

Example 11: SPIO-Labeled TRPV6-Binding Peptides Bind to TRPV6-Expressing Tumors but not to TRPV6-Negative Tumors Mice xenografted with a SKOV-3 TRPV6-rich ovarian tumor are administered SPIO-SorC27 and imaged using Magnetic Resonance Imaging.
Results The results show SPIO-conjugated TRPV6-binding peptides bind to TRPV6-rich tumors from human ovarian cancer cell line SKOV-3, and can imaged using Magnetic Resonance Imaging. Experiments show that ovarian tumors over-expressing the TRPV6 channel are detected in vivo by MRI enhancement agents such as SPIO-SorC27 after administration to the mouse. The TRPV6-rich xenografted tumor mass is clearly distinguished from the background tissue by strongly enhanced magnetic resonance signals and imaging.

Example 12: Use TRPV6-Binding Peptides Conjugated to $^{18}$F-Containing Radio-Molecules Compounds comprising TRPV6-binding peptides covalently labeled with $^{18}$F-containing radio-molecules target such molecules to TRPV6-expressing tumors, cells or tissues and allow for detection using PET scanning (Positron Emission Tomography) and detection of these tumors, cells or tissues (Cheng et al. J. Nucl. Med. 48:987-994, 2007). SorC27 conjugated with an $^{18}$F-containing radio-molecule is incubated with SKOV-3 cells and HEK293 cells. The cells are then imaged using PET scanning.
Results The $^{18}$F-SorC27 clearly shows the identification of the TRPV6-rich SKOV-3 cells as compared to TRPV6-negative cells (HEK293).

Example 13: Use TRPV6-Binding Peptides Conjugated to $^{125}$I-Containing Radio-Molecules Compounds comprising TRPV6-binding peptides covalently labeled with $^{125}$I-containing radio-molecules target such molecules to TRPV6-expressing tumors, cells or tissues and allow for detection using radiometric detection of these tumors, cells or tissues (Bolton et al. Biochem. J., 133, 529-539, 1973). SorC27 conjugated with a $^{125}$I-containing radio-molecule is incubated with SKOV-3 cells and HEK293 cells. The cells are then imaged using PET scanning.

Results

The $^{125}$I-C-peptide clearly shows the identification of the TRPV6-rich SKOV-3 cells as compared to TRPV6-negative cells (HEK293).

Example 14: Detection of TRPV6 mRNA in Microvesicles Isolated from Samples of Blood, Other Body Fluids or Excreta TRPV6 mRNA is detected in microvesicles isolated from samples of blood, other body fluids or excreta of patients with TRPV6-rich cancers (e.g. ovarian tumors). The fraction of blood containing microvesicles sloughed off of tumors through an endocytotic process is isolated from a sample obtained from a subject. RNA is then extracted from these microvesicles, with subsequent analysis by PCR-based techniques.

Results

Q-RT-PCR shows the presence of TRPV6 mRNA at excess in cancer patient blood samples in comparison to people without a TRPV6-rich cancer. Detection of relative amounts of TRPV6 expression is therefore useful to diagnose TRPV6-rich cancers such as ovarian cancer.

Example 15: Detection of TRPV6 Protein in Microvesicles Isolated from Bodily Fluids or Excreta TRPV6 protein is detected in microvesicles isolated from bodily fluids such as blood, lymph or excreta samples of patients with TRPV6-rich cancers (e.g. ovarian tumors). The fraction of the sample containing microvesicles sloughed off of tumors through an endocytotic process is isolated. Protein is then extracted from these microvesicles, with subsequent analysis by Western blotting and antibody-based techniques to detect TRPV6 protein. Alternatively, isolated microvesicles can be treated with either anti-TRPV6 antibodies or TRPV6-binding peptides and detected.

Results

Western blotting shows the presence of TRPV6 protein at excess in cancer patient blood samples in comparison to people without a TRPV6-rich cancer such as ovarian cancer. Whole microvesicles show TRPV6 by immunofluorescence using an antibody to TRPV6 and by using appropriately labeled TRPV6-binding peptides.

Example 16: In Vivo Use of TRPV6-Binding Peptides Conjugated to Taxanes

It is clear from the bio-distribution studies set out in Example 1 that the compounds comprising TRPV6-binding peptides are useful to deliver the attached fluorophore of the cyanidine class (cy5.5) to tissues, and to cells expressing TRPV6 (See FIGS. 6 to 9). Compounds comprising the TRPV6-binding peptides described herein may therefore be used to deliver other molecules to cells or tissues expressing TRPV6.

Compounds are prepared by covalent attachment of oncology drugs such as a taxanes to the TRPV6-binding peptides in order to use the TRPV6-targeting function of the peptides to deliver the drug directly to a TRPV6-rich tumor or cancer cell. The chemistry for attaching such drugs to compounds is known in the art (see for example, Peng Li et al., Biopolymers 87: 225-230, 2007).

Paclitaxel is attached through a four carbon spacer molecule to the SorC27 peptide at a primary amine or free thiol group. The SorC27-conjugated taxane is then administered to mice xenografted with a TRPV6-rich tumor. Control mice are administered saline solution.

Results

In vivo experiments in mice show that a compound comprising a TRPV6-binding peptide conjugated to paclitaxel results in the adequate delivery of paclitaxel to the tumor site, regression of the tumor and the death of cancer cells when compared to control mice administered saline solution.

Example 17: Delivery of Anti-Viral Drugs Conjugated to TRPV6-Binding Peptides

Anti-viral or anti-retroviral drugs are readily covalently attached to TRPV6-binding peptides for the treatment of reservoirs of HIV. A primary reservoir of HIV in humans is the mesenteric lymph nodes (Cumont et al. Cell Death and Differentiation, 14, 1747-1758, 2007; Estaquier and Hurtrel. Medical Science (Paris) 24(12): 1055-1060, 2008). Compounds comprising the TRPV6-binding peptides carrying a fluorescent tag accumulate in the mesenteric lymph nodes as shown by the presence of fluorescence in these nodes after i.v. injection of the tagged peptide (see FIG. 1).

Anti-viral or anti-retrovirals are covalently attached to the TRPV6-binding peptides described herein. A compound comprising a SorC27-anti-viral conjugate is then administered to mice following the protocol set out in Example 1.

Results

The results show the anti-viral conjugate is detected in lymph node tissue. Anti-viral activity is obtained, blocking HIV reproduction and thereby treating HIV.

Example 18: TRPV6-Binding Peptides Conjugated to Anti-Microbials

The covalent attachment of anti-microbial drugs to the TRPV6-binding peptides is useful for the treatment of reservoirs of bacterial infection. Compounds comprising the TRPV6-binding peptide conjugated to a fluorescent tag accumulate in the lymph nodes as indicated by the presence of fluorescence in these nodes after iv injection of the tagged peptide (see FIG. 1). Similarly, anti-microbials are optionally covalently attached to the TRPV6-binding peptides by methods known in the art, and used to target lymph nodes.

Results

The results show that the drugs are detected in lymph node tissue isolated from mice treated with the anti-microbial-TRPV6-binding conjugates and will kill microbes.

Example 19: TRPV6-Binding Peptides Conjugated to Boron Complexes

Compounds comprising a boron complex covalently attached to a TRPV6-binding peptide are useful for cancer therapy. The TRPV6-binding peptides target and contact TRPV6-rich cells and tumors causing concentration of the boron complexes therein (each with multiple boron atoms, for example the 12 boron closo-boron complex). Irradiation with thermal neutrons results in neutron capture by boron-10 atoms and transfer of high energy alpha-particles to the tissue killing tumor cells. This aspect of the invention provides for large amounts of boron clusters being targeted to tumors. The threshold has been stated to be about 20 ug B/g tumor (Barth et al. Clinical Cancer Research, 11 (11) 3987-4002, 2005). The chemistry to attach boron compounds to protein complexes is a well established (Guan et al. Proc. Natl. Acad. Sci., 95 13206-13210, 1998). Boron conjugated to TRPV6-binding peptides is administered to mice xenografted with a TRPV6-rich tumor. The tumor is then irradiated with thermal neutrons.

Results

The concentration of boron is greatly increased in TRPV6-rich tumors such as ovarian tumors. Irradiation of the tumor with thermal neutrons kills the tumor cells. The boron-peptide compounds are useful for killing tumor cells.

Example 20: TRPV6-Binding Peptides Conjugated to Epitopes

The covalent attachment of known and/or recognized epitopes of global antibodies to the TRPV6-binding peptides recruit these pre-existing antibodies to TRPV6-expressing tumors and cancer cells. This complex (antibody-epitope-TRPV6-binding peptide) results in detection and destruction of TRPV6-expressing cells by immune cells as shown in xenograft experiments where tumors (e.g. ovarian) had lower growth rates.

Example 21: TRPV6-Binding Peptides Conjugated to Antigens or Epitopes

The covalent attachment of a novel antigen or epitope to the TRPV6-binding peptides and administration of the compound to mice directs the epitope/TRPV6-binding peptide complex to the TRPV6-bearing tumors. Subsequent administration of a monoclonal or polyclonal antibody directed against the specific epitope results in either type of antibody attaching to the TPRV6-rich cell, tissue or tumor. Subsequent recruitment of immune cells (e.g. killer T-cells) results in death of these peptide-targeted cells and shrinkage of the tumors.

Example 22: TRPV6-Binding Peptides Conjugated to Immunoactivators

The covalent attachment of TRPV6-binding peptides and a molecule that is recognized and bound by receptors on cells of the immune system, particularly killer T-cells, directs such cells to TRPV6-rich tumors or cancer cells. The recruitment of such cells as killer T-cells destroy the cancer cell or tumor. The experiments indicate that the TRPV6-binding peptide targets the TRPV6 channel while the 'bate molecule' attached to the other end of the TRPV6-binding peptides recruits the immune cell; administration of this product causes shrinkage of tumors (e.g. xenografted ovarian tumors).

Example 23: TRPV6-Binding Peptides Conjugated to Metallic Nano-Structures

The covalent attachment of metallic nano-structures (e.g. nano-gold particles) to the TRPV6-binding peptides targets the metal nano-particles or other constructs (spheres, rods etc.) through the TRPV6 binding function of the peptides, to cancer cells and tumors. Because of the unique properties of, for example, nano-gold particles, irradiation with radio frequencies or infrared radiation cause the particles to heat up. Subsequent heating of the cancer cell or tumor causes death of the cells or tumor. The chemistry to attach metallic nano-particles to molecules such as peptides, is well established. Experiments indicate that targeting of the nano-gold conjugate, to TRPV6-rich xenografted tumors (e.g. ovarian tumors), with subsequent irradiation causes shrinkage of the tumor mass.

Example 24: Use of TRPV6 Antibodies to Detect and Grade Cancer

Samples comprising tissue sections of 146 independent biopsies over 4 tissue micro-arrays (TMA) (OV483, OV802, T112, BCN721 obtained from US Biomax, Inc. Rockville, Md. 20850, USA) were tested for immunohistochemical staining of TRPV6 using a TRPV6 antibody, secondary antibody and colorimetric detection using horseradish peroxidase (HRP). The samples included eighteen different ovarian cancer types representing all the major types of ovarian cancers as well as 21 samples of normal ovarian tissues. Many of the samples represented cancers that were previously graded. FIG. 17 shows the calibration and representative grading of TMA samples on a six-point scale from (−) to (++++) used to assess intensity of TRPV6 staining. As shown in Table 3, each of the 146 samples was ranked according to this six-point scale.

FIG. 18 shows that a much smaller percentage of normal ovarian tissue samples had a TRPV6 stain intensity score ≥1+ compared to serous papillary adenocarcinoma tissue samples with grade I, grade II, or grade III cancer. For example, 100% of serous papillary adenocarcinoma tissue samples had a stain intensity score of ≥1, compared with only about 24% of normal ovarian tissues. Accordingly, detection of TRPV6 such as by antibody staining is useful in order to predict or diagnose the likelihood of cancer in a sample. Furthermore, detection of TRPV6 is useful to identify samples with Grade I (early stage) cancer compared to normal ovarian tissue samples.

FIG. 19 shows examples of the immunohistochemical detection of TRPV6 using TRPV6 antibodies in micro-array samples of normal ovarian tissues, as well as samples of Grades I, II and III serous papillary carcinoma. FIG. 19 shows an observed trend of increased staining of TRPV6 in samples with higher Grades of cancer.

Cancer staging data was also available for a number of tissue array samples. Cancers were staged according to the Tumor, Node, Metastasis (TNM) system as known in the art. TRPV6 immunohistochemical staining intensity for each sample assessed on a five-point scale from (−) to (++++) using a TRPV6 antibody, secondary antibody and colorimetric detection using horseradish peroxidase (HRP) is provided in Table 4.

As shown in Table 4, only 23.8% (5/21) of normal ovarian tissue samples had a TRPV6 stain intensity score greater than or equal to +1. In contrast, 95.7% (44/46) of samples with stage I-IV cancer had a TRPV6 intensity score greater than or equal to +1. Early stage cancers (stage I and stage II) were readily detected with 92.9% (26/28) of early stage cancers having a TRPV6 stain intensity score greater than or equal to +1. Detection of TRPV6, such as by immunohistochemical methods, can therefore be used to detect cancer and in particular early stage cancers.

TABLE 3

Ovarian carcinoma and normal tissue array TRPV6 staining in 146 samples.

| Pathology Diagnosis | Total Case Number | TRPV6 IHC Results (Stain Intensity) | | | | | |
|---|---|---|---|---|---|---|---|
| | | − | −/+ | + | ++ | +++ | ++++ |
| Normal ovarian tissue | 21 | 8 | 8 | 3 | 2 | 0 | 0 |
| Mucinous papillary | | | | | | | |

TABLE 3-continued

Ovarian carcinoma and normal tissue array TRPV6 staining in 146 samples.

| Pathology Diagnosis | Total Case Number | TRPV6 IHC Results (Stain Intensity) | | | | | |
|---|---|---|---|---|---|---|---|
| | | − | −/+ | + | ++ | +++ | ++++ |
| adenocarcinoma | | | | | | | |
| Total | 12 | 1 | 0 | 3 | 0 | 4 | 4 |
| Grade I | 2 | 0 | 0 | 0 | 0 | 1 | 1 |
| Grade II | 7 | 1 | 0 | 1 | 0 | 2 | 3 |
| Grade III | 3 | 0 | 0 | 2 | 0 | 1 | 0 |
| Mucinous papillary cystadenocarcinoma | | | | | | | |
| Total | 14 | 2 | 0 | 2 | 4 | 4 | 2 |
| Grade I | 11 | 2 | 0 | 2 | 3 | 4 | 0 |
| Grade II | 3 | 0 | 0 | 0 | 1 | 0 | 2 |
| Serous papillary adenocarcinoma | | | | | | | |
| Total | 58 | 0 | 0 | 7 | 13 | 18 | 20 |
| Grade I | 8 | 0 | 0 | 2 | 2 | 0 | 4 |
| Grade II | 22 | 0 | 0 | 1 | 6 | 8 | 7 |
| Grade III | 28 | 0 | 0 | 4 | 5 | 10 | 9 |
| Serous papillary cystadenocarcinoma | | | | | | | |
| Total (Grade III) | 3 | 0 | 0 | 0 | 1 | 2 | 0 |
| Clear cell carcinoma | 9 | 0 | 0 | 1 | 6 | 2 | 0 |
| Endometroid adenocarcinoma | 4 | 0 | 0 | 0 | 0 | 3 | 1 |
| Transitional cell carcinoma | 1 | 0 | 0 | 0 | 0 | 1 | 0 |
| Granular cell tumor | 3 | 0 | 1 | 2 | 0 | 0 | 0 |
| Endodermal sinus carcinoma | 2 | 0 | 0 | 0 | 0 | 0 | 2 |
| Squamous cell carcinoma | 1 | 0 | 0 | 0 | 0 | 1 | 0 |
| Metastatic signet-ring cell carcinoma | 3 | 0 | 0 | 1 | 1 | 1 | 0 |
| Metastatic adenocarcinoma | 6 | 0 | 0 | 0 | 0 | 2 | 4 |
| Mixed germ cell tumor | 1 | 0 | 0 | 0 | 0 | 1 | 0 |
| Malignant follicular theca cytoma | 1 | 0 | 0 | 0 | 1 | 0 | 0 |
| Malignant tumor (sparse) | 2 | 0 | 0 | 0 | 2 | 0 | 0 |
| Dysgerminoma | 3 | 0 | 0 | 0 | 2 | 1 | 0 |
| Immature teratoma | 1 | 0 | 0 | 1 | 0 | 0 | 0 |
| Hyperplastic fibrous tissue | 1 | 0 | 0 | 1 | 0 | 0 | 0 |

TABLE 4

Ovarian carcinoma and normal tissue arrays grouped by cancer stage. Total number of cases = 67; total number of tumor samples = 46.

| Pathology Diagnosis | Total Case Number | TRPV6 IHC Results (Stain Intensity) | | | | |
|---|---|---|---|---|---|---|
| | | − | + | ++ | +++ | ++++ |
| Normal ovarian tissue | 21 | 16 | 3 | 2 | 0 | 0 |
| Mucinous papillary adenocarcinoma | | | | | | |
| Total | 11 | 1 | 3 | 0 | 3 | 4 |
| Stage I | 5 | 0 | 0 | 0 | 2 | 3 |
| Stage II | 1 | 1 | 0 | 0 | 0 | 0 |
| Stage III | 3 | 0 | 1 | 0 | 1 | 1 |
| Stage IV | 2 | 0 | 2 | 0 | 0 | 0 |
| Mucinous papillary cystadenocarcinoma | | | | | | |
| Total | 12 | 1 | 2 | 4 | 4 | 1 |
| Stage I | 9 | 1 | 1 | 3 | 3 | 1 |
| Stage II | 1 | 0 | 0 | 0 | 1 | 0 |
| Stage III | 1 | 0 | 1 | 0 | 0 | 0 |
| Stage IV | 1 | 0 | 0 | 1 | 0 | 0 |
| Serous papillary adenocarcinoma | | | | | | |
| Total | 15 | 0 | 2 | 5 | 3 | 5 |
| Stage I | 7 | 0 | 1 | 3 | 0 | 3 |
| Stage II | 2 | 0 | 0 | 0 | 1 | 1 |
| Stage III | 6 | 0 | 1 | 2 | 2 | 1 |
| Stage IV | 0 | 0 | 0 | 0 | 0 | 0 |
| Clear cell carcinoma (Stage I) | 3 | 0 | 2 | 1 | 0 | 0 |
| Endometroid adenocarcinoma | 4 | 0 | 0 | 0 | 3 | 1 |
| Transitional cell carcinoma | 1 | 0 | 0 | 0 | 1 | 0 |

Example 25: Co-Localization of TRPV6 and Fluorescently-Labeled Sorc27 in Grade II Serous Papillary Adenocarcinoma To test the efficacy of tagged SorC27 peptide to detect its binding target TRPV6, standard immunohistochemical and SorC27-cy5.5 binding protocols were applied to tissue micro-arrays of a number of ovarian cancer tumor sections. The detection of TRPV6 channel by both methods was observed across different ovarian cancer microarray samples.

Results

FIG. 20 shows TRPV6 antibody detection and fluorescent detection a tissue micro-array sample of grade II serous papillary adenocarcinoma stained with antibodies to TRPV6 as well as SorC27 fluorescently labeled with cy5.5 (SorC27-cy5.5). The use of fluorescently-labeled TRPV6-binding peptides therefore corresponds to the standard immunohistochemical detection of TRPV6 ion channels and TRPV6-binding peptides are useful to reliably detect TRPV6 or cells or tissues that express TRPV6.

Example 26: Localization of SorC27 to Xenografted Cancer Tumors In Vivo

Mice xenografted with a TRPV6-rich ovarian (SKOV-3 cells) and prostate (DU145 cells) tumors were injected (intraperitoneally) with the fluorescently-labeled TRPV6-binding peptide SorC27-cy5.5. SorC27 was labeled with the near-infrared probe Cy5.5 at the single cysteine thiol using a Cy5.5 maleimide-activated reaction. The labeled peptides were purified with a combination of size exclusion chromatography and HPLC. Cy5.5, fluoresces in the infra-red region after excitation with a scanning laser. The low energy laser is able to penetrate the animal to about 1 cm and, thus, by scanning, the presence of the tagged peptides can be quantified in three dimensions. Cy5.5-labeled peptides were intraperitoneally injected into nude CD1 mice at 100 ug per animal, and animals were imaged live using an optical imaging system, Optix eXplorer (GE Healthcare Systems) at different time points (30 min, 90 min, 4 h).

Results

The ovarian and prostate tumors over-expressing the TRPV6 channel are clearly detected in vivo for at least 24 hours after injection. The TRPV6-rich xenografted tumor masses are clearly distinguished from the background tissue as strongly fluorescing in the far infrared. FIG. 21A shows the time dependent localization of SorC27-cy5.5 in ovarian tumor, while FIG. 21B shows the time dependent localization of SorC27-cy5.5 in prostate tumor. The kidneys are also highlighted in these two images. The 3-D nature of the scanning device allows clear discrimination between the tumors and the visible kidney tissues by isolating a 2 mm slice of the animal. As well, a 'slice' through the tumor (the Z-slice) allows clear observation of the fluorescing central region of the tumors.

Example 27: Quantitative RT-PCR of TRPV6 mRNA in Cancer Tissues

Quantitative RT-PCR for TRPV6 mRNA was performed on samples of ovarian, prostate and breast cancer biopsies as well as corresponding pooled control samples from 15 healthy individuals. 18 ovarian tumor biopsies, 4 prostate tumor biopsies, and 3 breast tumor biopsies were tested. 3 different RT-PCR primer sets (A, B and C) were used for testing of the prostate samples. Results were standardized against the expression levels of the housekeeping gene hypoxanthine phosphoribosyl transferase (HPRT) and expressed as a ratio of the standardized signal from the tumor samples to the standardized signals from a pooled sample of 15 healthy tissues.

Results

FIG. 22 shows the results of Q-RT-PCR quantification of TRPV6 mRNA extracted from human ovarian (A), prostate (B) and breast cancer biopsies (C), compared to healthy tissues. Tables 5 to 7 also provide the quantitative Q-RT-PCR results for each of the sample biopsies relative to normal controls. Tumor biopsies showed a significant increase in expression levels of TRPV6 mRNA. Increases in TRPV6 mRNA expression relative to control tissues were seen in each cancer sample tested except one ovarian cancer sample (LTL290). Ovarian cancer samples showed an average 39 times increase in the expression of TRPV6 mRNA compared to healthy controls, while prostate cancer samples and breast cancer samples exhibited 8.7 times and 13 times increases respectively. The significant increases observed in transcription of TRPV6 mRNA in cancer tissues provides a useful diagnostic or prognostic tool for identifying cancer including ovarian, breast and/or prostate cancers.

TABLE 5

TRPV6 mRNA quantitative RT-PCR results for ovarian cancer biopsies.

| Sample ID | Average Relative Increase in TRPV6 mRNA Expression | S.D | n |
|---|---|---|---|
| LTL175 | 2.93 | 0.6 | 3 |
| LTL205 | 10.08 | 1.7 | 3 |
| LTL234 | 12.04 | 1.0 | 3 |
| LTL237 | 17.62 | 3.3 | 3 |
| LTL246 | 5.94 | 0.0 | 3 |
| LTL247 | 41.52 | 3.0 | 3 |
| LTL258 | 4.54 | 0.1 | 3 |
| LTL259 | 4.55 | 1.4 | 3 |
| LTL260 | 4.87 | 0.4 | 3 |
| LTL269 | 14.56 | 0.6 | 3 |
| LTL273 | 12.44 | 0.3 | 3 |
| LTL284 | 13.49 | 1.6 | 3 |
| LTL290 | 0.44 | 0.0 | 3 |
| LTL300 | 101.15 | 9.1 | 3 |
| LTL305 | 13.42 | 3.0 | 3 |
| LTL315 | 72.90 | 7.0 | 3 |
| LTL317 | 20.23 | 1.2 | 3 |
| LTL320 | 354.02 | 33.8 | 3 |

TABLE 5-continued

TRPV6 mRNA quantitative RT-PCR results for ovarian cancer biopsies.

| Sample ID | Average Relative Increase in TRPV6 mRNA Expression | S.D | n |
|---|---|---|---|
| Average | 39.3 | | |
| Median | 12.9 | | |

S.D. = standard deviation; n = number of samples.

TABLE 6

TRPV6 mRNA quantitative RT-PCR results for prostate cancer biopsies. Average and median taken for all primer sets across each sample.

| | Relative Increase in TRPV6 mRNA Expression | | |
|---|---|---|---|
| Sample ID | Primer Set A | Primer Set B | Primer Set C |
| A5 | 12.3 | 4.9 | 5.4 |
| A11 | 20.8 | 5.9 | 9.6 |
| A12 | 9.1 | 2.4 | 5.6 |
| PA-T | | 16.3 | 3.1 |
| Average | | 8.7 | |
| Median | | 5.9 | |

TABLE 7

TRPV6 mRNA quantitative RT-PCR results for breast cancer biopsies.

| Sample ID | Relative Increase in TRPV6 mRNA Expression |
|---|---|
| FBT-1 | 22.5 |
| FBT-2 | 3.6 |
| FBT-3 | 12.9 |
| Average | 13 |

Example 28: In Vivo Injection and MRI Imaging of TRPV6-Binding Peptide Conjugates (SPIO-SorC27)

Conjugation of SorC27 to SPIO Nano-Beads

SPIO (Super Paramagnetic Iron Oxide) beads functionalized with approximately 120 maleimide groups per bead (Product No. 77-96-201 from micromod Partikeltechnologie GmbH, Germany) were reacted with a 5-fold molar excess of buffered Sor-C27 (1 mM, 10×PBS, pH 7.2) for 1 hour at room temperature. The beads were separated from the reaction mixture by centrifugation and suspended in a volume of sterile Dulbecco's PBS for injection into the tumor-bearing CD-1 nude mice. The number of SOR-C27 peptides per bead was determined by quantitative $^1$H NMR analysis of the supernatant to determine number of reacted peptide molecules. On average 75 molecules of SOR-C27 were conjugated to each SPIO particle. Conjugation of the peptide to the SPIO was confirmed by LC-MS after trypsin digest of the SPIO-peptide conjugate. The SPIO-SorC27 conjugate was then injected intraperitoneally (i.p.) into SKOV-3 derived ovarian tumors xenografted into CD-1 nude mice prior to imaging.

MRI Image Capture

The MRI images were acquired on a 3T Varian Direct Drive Console using a 305/210 mm OD/ID Magnex gradient coil and a 25 mm diameter quadrature mouse RF coil from Doty Inc. The images were acquired using a pulse sequence specifically selected to optimize contrast sensitivity to iron-oxide nanoparticles. The iron-oxide appears dark (negative contrast) for these types of acquisitions. The acquisitions used a 3D balanced steady state free precession (b-SSFP) pulse sequence with a TR/TE of 8/4 ms and an image resolution of 150 micron (150 micron pixel dimension in all 3 directions).

Results

FIG. 23 shows MRI images and the localization of the MRI enhancement agent (SPIO-SorC27) to SKOV-3 derived ovarian tumors xenografted into CD-1 nude mice. The upper control panels (A) show the administration of the SPIO control beads, without conjugated SorC27. The SPIO control beads were cleared from the tumor by 24 hours post-injection. The lower level panel (B) shows that the SPIO-SorC27 compound labels the cortex of the tumor 24 hours post-injection. The solid white arrow shown in the left-hand images indicates the position of the tumor in the xenograft. The dashed arrow in the bottom right panel indicates the darkened enhanced MRI signal of the SPIO-SorC27 construct bound to the cortex of the tumor. No corresponding accumulation of the iron nano-particles is observed in the top right control panel. The panels on the right hand side show MRI imaging before i.p. injection, while those on the right-hand side show MRI imaging 24 hours after administration of the control or diagnostic reagent. Conjugated TRPV6-binding peptides such as SorC27-conjugates are therefore able to effectively target tumor sites in vivo.

Example 29: RT-PCR of Blood from Staged Cancer Subjects

Samples of blood taken from subjects with prostate, breast or ovarian cancer (stages I to IV) were tested for TRPV6 mRNA expression using RT-PCR. Control samples of blood taken from a healthy male (prostate) or healthy female (breast and ovarian) were also tested. RT-PCR products were loaded onto agarose gels and separated using electrophoresis. Integrated band density was then measured on the agarose gels for the amplicons of the TRPV6 mRNA (~320 bp) for each sample and control.

Results

Figure 24C:
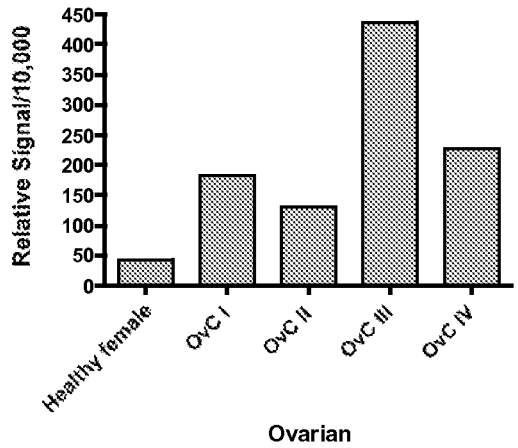

FIG. 24 shows that the expression of TRPV6 mRNA in blood samples taken from patients with cancer was significantly higher compared to samples taken from normal healthy controls. FIG. 24A shows that subjects with stage I, II, III or IV prostate cancer had up to 6 times more expression of TRPV6 in blood. A significant increase in TRPV6 expression is also seen in samples representing different cancer stages compared to normal samples. FIG. 24B shows that subjects with breast cancer exhibit a significant increase in blood TRPV6 expression. FIG. 24C shows that subjects with ovarian cancer also exhibit an increase in TRPV6 expression compared to healthy female control samples. The integrated signals represented in FIG. 24 were divided by a factor of either 100,000 (24A & 24B) or 10,000 (24C). Analysis of expression levels of TRPV6 mRNA in blood is therefore useful to identify subjects with cancer, including the early detection of stage I prostate, breast or ovarian cancer.

Example 30: TRPV6 mRNA in Plasma Samples from Subjects with Stage I or Stage II Ovarian Cancer Total RNA was extracted from plasma samples from healthy women (10) and from women with Stage I (3) or Stage II (3) ovarian cancer using the TRI Reagent® LS method (Sigma Aldrich). After preparation of cDNA libraries (iScript, BioRad) from an equal amount of the extracted RNA from each sample, the samples were subjected to standard PCR. PCR reactions were analyzed using E-Gel® EX 1% agarose gels and run on the E-Gel® iBase gel electrophoresis unit. Using Program 7, for E-Gel® EX 1-2% gels, for 10 mins. The TRPV6 mRNA (cDNA) amplicons were imaged and quantified with an Alpha Innotech FluorChem® FC2 imager, using filter position #1 (green filter) and UV light (302 nm) using Auto Expose. All samples were analyzed in triplicate and data were compared using the Student's t-test and the 95% confidence limit.

Results

As shown in FIG. 25, plasma taken from subjects with stage I or II ovarian cancer had significantly more expression of TRPV6 mRNA ($p<0.0001$ OVI; $p=0.0475$ OVII) compared samples from healthy controls.

Example 31: Analysis of TRPV6 Protein Levels in Subjects with Stage I and II Ovarian Cancer Plasma samples were obtained from healthy women and women diagnosed with stage I or II ovarian cancer. Protein was isolated from the plasma samples following the TRI Reagent® LS method (Sigma Aldrich). Lysates were prepared from the plasma protein pellets from the TRI Reagent® LS procedure by heating in a solution of 1% SDS in PBS and 15 mM dithiothreitol (DTT) in a boiling water bath. Protein extracts were quantified by measuring the absorbance at 280 nm of each lysate on a Varian Cary 50 UV spectrophotometer. The amount of protein in ug/uL was extrapolated from a bovine serum albumin protein standard curve. Protein extracts were electrophoresed on NuPage® Novex 4-12% Bis-Tris Gel 1.5 mm wells (Invitrogen) at 145V for 55 mins. The gels were transferred for 10 mins onto a iBlot® Transfer Stack, PVDF regular (Invitrogen) using the Invitrogen iBlot transfer system. PVDF blocking, antibody incubation and washing were performed using a SNAP i.d. protein detection system (Millipore). The PVDF membranes were then blocked for 30 seconds with 0.5% ECL advanced blocking buffer (Fisher). The PVDF's were incubated in a 1/30 dilution of TRPV6 (H-90) primary antibody (Santa Cruz) for 10 min and washed 3 times with 30 mL of TBS-T. The PVDFs were then incubated in a 1/1500 dilution of goat anti-rabbit IgG HRP secondary antibody (Santa Cruz) for 10 min and washed 3 times with 30 mL of TBS-T. The TRPV6 bands were detected with 15 ml of Luminol for 3 mins. Gels were imaged and the band density was quantified with an Alpha Innotech FluroChem imager for 10 minutes. All samples were analyzed in triplicate and data were compared using the Student's t-test and the 95% confidence limit.

Results

As shown in FIG. 26A, the levels of TRPV6 protein were significantly higher in blood samples taken from subjects with stage I ($p=0.0001$) or stage II ($p=0.0270$) ovarian cancer compared to samples take from healthy controls. FIG. 26B shows that stage I and stage II ovarian cancer considered together (early stage cancers) also exhibit increased levels of TRPV6 protein ($p=0.0006$) compared to healthy controls.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Aalders J. G., Thomas G. 2007. Endometrial cancer—revisiting the importance of pelvic and para aortic lymph nodes. Gynecol. Oncol. 104(1): 222-231. Review Agnes, R. S., Lee, Y. S., Davis, P., Ma, S. W., Badghisi, H., Porreca, F., Lai, J., Hruby, V. J. 2006. Structure-activity relationships of bifunctional peptides based on overlapping pharmacophores and opioid and cholescytokinin receptors. Journal of Medicinal Chemistry, 49: 2868-2875.

Barth, R. F., Coderre, J. A., Graca, M., Vicente, H., Blue, T. E. 2005. Boron neutron capture therapy of cancer: current status and future prospects. Clinical Cancer Research, 11: 3987-4002.

Bolton, A. E. and Hunter, W. M. 1973. The labeling of proteins to high specific radioactivities by conjugation to a $^{125}$I-containing acylating agent. Biochem. J., 133: 529-539.

Cheng. Z., Zhang, L., Graves, E., Xiong, Z., Dandekar, M., Chen, X. Gambhir S. S. 2007. Small-animal PET of malanocortin 1 receptor expression using a $^{18}$F-labeled α-melanocyte stimulating hormone analog. J. Nucl. Med. 48: 987-994.

Cumont, M. C., Monceaux, V., Viollet, L., Lay, S., Parker, R., Hurtrel, B. Estaquier, J. 2007. TFG-b in intestinal lymphoid organs contributes to the death of armed effector CD8 T cells and is associated with the absence of virus containment in rhesus macaques infected with the simian immunodeficiency virus. Cell Death and Differentiation, 14: 1747-1758.

den Dekker, E., Hoenderop, J. G. J., Nilius, B., Bindels, R. J. M. 2003. The epithelial calcium channels, TRPV5 & TRPV6: from identification towards regulation. Cell Calcium, 33: 497-507.

Estaquier, J. Hurtrel, B. 2008. Mesenteric lymph nodes, a sanctuary for the persistence of HIV. Medical Science (Paris) 24(12): 1055-1060.

Guan, L., Wims, L. A., Kane, R. R., Smuckler, M. B., Morrison, S. L. Hawthorne, M. F. 1998. Homogeneous immunoconjugates for boron neutron-capture therapy: Desing, synthesis, and preliminary characterization. Proc. Natl. Acad. Sci., 95: 13206-13210.

Lu, P., Boros, S., Chang, Q., Bindels, R. J., Hoenderop, J. G. 2008. The beta-glucuronidase klotho exclusively activates the epithelial $Ca^{2+}$ channels TRPV5 and TRPV6. Nephrol. Dial. Transplant, 23: 3397-3402.

Lyshchik, A., Higashi, T., Asato, R., Tanaka, S., Ito, J., Hiraoka, M., Insana, M. F., Brill, A. B., Saga, T., Togashi, K. 2007. Cervical lymph node metastases: diagnosis at sonoelastography—initial experience. Radiology. 243(1): 258-267.

Ma, J., Liu, L., Tang, L., Zong, J., Lin, A., Lu, T., Cui, N., Cui, C., Li, L. 2007. Retropharyngeal lymph node metastasis in nasopharyngeal carcinoma: prognostic value and staging categories. Clin. Cancer Res. 13(5): 1445-1452.

Mujoomdar, A., Austin, J. H., Malhotra, R., Powell, C. A., Pearson, G. D., Shiau, M. C., Raftopoulos, H. 2007. Clinical predictors of metastatic disease to the brain from non-small cell lung carcinoma: primary tumor size, cell type, and lymph node metastases. Radiology. 242(3): 882-888.

Peng, J., Chen, X., Berger, U. V., Weremowicz, S., Morton, C. C., Vassilev, P. M., Brown, E. M., Hediger, M. A. 2000. Human Calcium Transport Protein CaT1. Biochim. Biophys. Res. Comm. 278: 326-332. [Note: CaT1=TRPV6]

Peng, L., Jiang, S. Pero, S. C., Olingino, L. Krag, D. N., Michejda, C. J., Roller, P. P. 2007. Design and synthesis of paclitaxel conjugated with an ErbB2-Recognizing peptide, EC-1. Biopolymers, 87: 225-230.

Veness, M. J., Porceddu, S., Palme, C. E., Morgan, G. J. 2007. Cutaneous head and neck squamous cell carcinoma metastatic to parotid and cervical lymph nodes. Head Neck. 29(7): 621-631. Review.

Vernooij, F., Sie-Go, D. M., Heintz, A. P. 2007. Lymph node recurrence following stage IA vulvar carcinoma: two cases and a short overview of literature. Int. J. Gynecol. Cancer. 17(2): 517-520. Review.

Wind, J., Lagarde, S. M., Ten Kate, F. J., Ubbink, D. T., Bemelman, W. A., van Lanschot, J. J. 2007. A systematic review on the significance of extracapsular lymph node involvement in gastrointestinal malignancies. Eur. J. Surg. Oncol. 33(4): 401-408. Review.

Yamamoto, T., Nair, P., Vagner, J., Largent-Milnes, T., Davis, P., Ma, S. W., Navratilova, E., Moye, S., Tumati, S., Lai, J., Yamamura, H. I., Vanderah, T. W., Porreca, F., Hruby, V. J. 2008. A structure-activity relationship study of combinatorial synthetic approach of C-terminal modified bifunctional peptides that are delt/mu opioid receptor agonists and neurokinin 1 receptor antagonists. J. of Med. Chem. 51(5): 1369-1376.

Zhuang, L., Peng, J-B., Tou, L., Takanaga, H., Adam, R. M., Hediger, M. A., Freeman, M. R. 2002. Calcium-Selective Ion Channel, CaT1, Is Apically Localized in Gastrointestinal Tract Epithelia and Is Aberrantly Expressed in Human Malignancies. Laboratory Investigation. 82(12): 1755-1764.

The invention claimed is:

1. A compound, comprising a Transient Receptor Potential Vanilloid 6 (TRPV6)-binding peptide conjugated to a metal chelate and comprising a radioisotope, wherein the TRPV6-binding peptide does not exhibit paralytic activity and:
   a) comprises from 9 to 27 contiguous C-terminal amino acids of SEQ ID NO:1;
   b) has an amino acid sequence with at least 90% identity to HPSKVDLPR;
   c) has an amino acid sequence with at least 90% identity to KEFLHPSKVDLPR; or
   d) has an amino acid sequence with at least 90% identity to EGKLSSNDTEGGLCKEFLHPSKVDLPR.

2. The compound of claim 1, wherein the TRPV6-binding peptide comprises the amino acid sequence HPSKVDLPR, KEFLHPSKVDLPR, or EGKLSSNDTEGGLCKEFLHPSKVDLPR.

3. The compound of claim 1, wherein TRPV6-binding peptide consists of from 9 to 27 contiguous C-terminal amino acids of SEQ ID NO: 1.

4. The compound of claim 1, wherein the TRPV6-binding peptide:
   i) consists of 9 to less than 27 amino acids; or
   ii) consists of the amino acid sequence HPSKVDLPR, KEFLHPSKVDLPR, or EGKLSSNDTEGGLCKEFLHPSKVDLPR.

5. The compound of claim 1, wherein the TRPV6-binding peptide has an amino acid sequence with at least 90% identity to KEFLHPSKVDLPR.

6. A pharmaceutical composition comprising the compound of claim 1 and a pharmaceutically acceptable carrier.

7. A method for detecting TRPV6 protein in a tissue comprising:
   a) contacting the tissue with the compound of claim 1;
   b) detecting the radioisotope conjugated to the TRPV6-binding peptide, thereby detecting the TRPV6 protein.

8. The method of claim 7, wherein the radioisotope is detected in vivo, ex vivo, or in vitro.

9. A method of identifying cancer in a sample from a subject, comprising detecting TRPV6 protein in the sample, wherein detecting TRVP6 protein in the sample comprises contacting the sample with the compound of claim 1 and detecting the radioisotope conjugated to the TRPV6-binding peptide, wherein increased levels of the TRPV6 protein in the sample compared to a control are indicative of the cancer.

10. The method of claim 9, wherein the sample is a bodily fluid optionally selected from blood, plasma, lymph, urine, and saliva.

11. The method of claim 9, wherein the cancer is stage I cancer or stage II cancer, optionally ovarian cancer or breast cancer.

12. A method for identifying a cancerous tumor in a subject, comprising
   a) administering to the subject a compound comprising a TRPV6-binding peptide of claim 1;
   b) detecting the radioisotope in the subject, thereby detecting TRPV6; and
   c) identifying regions of the subject with increased levels of TRPV6 relative to a control level, wherein increased levels of TRPV6 are indicative of a cancerous tumor, thereby identifying a cancerous tumor in the subject.

13. The method of claim 12, further comprising d) administering to the subject with the cancerous tumor a compound comprising a TRPV6-binding peptide conjugated to a metal chelate and comprising a radioisotope.

14. The method of claim 9, further comprising administering to the subject a compound comprising a TRPV6-binding peptide conjugated to a metal chelate and comprising a radioisotope.

* * * * *

UNITED STATES PATENT AND TRADEMARK OFFICE
CERTIFICATE OF CORRECTION

PATENT NO. : 11,090,396 B2
APPLICATION NO. : 16/046786
DATED : August 17, 2021
INVENTOR(S) : John M. Stewart It is certified that error appears in the above-identified patent and that said Letters Patent is hereby corrected as shown below:

In the Claims

Column 40, Claim 10, Line 34:
"fluid optionally selected from blood, plasma, lymph, urine,"
Should read:
-- fluid selected from blood, plasma, lymph, urine, --

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 2

<210> SEQ ID NO 1
<211> LENGTH: 27
<212> TYPE: PRT
<213> ORGANISM: Artificial Sequence
<220> FEATURE:
<223> OTHER INFORMATION: Synthetic peptide

<400> SEQUENCE: 1
```

```
Glu Gly Lys Leu Ser Ser Asn Asp Thr Glu Gly Gly Leu Cys Lys Glu
1               5                   10                  15

Phe Leu His Pro Ser Lys Val Asp Leu Pro Arg
            20              25

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide

<400> SEQUENCE: 2

Ser Ile Leu Ala Arg Pro Ala Glu Leu Asn Thr Glu Thr Cys Ile Leu
1               5                   10                  15

Glu Cys
```